(12) United States Patent
Sun et al.

(10) Patent No.: US 12,403,116 B2
(45) Date of Patent: Sep. 2, 2025

(54) HYDROXYPENTYL BENZOIC ACID DIESTER COMPOUND, AND PREPARATION METHOD AND PHARMACEUTICAL APPLICATION THEREOF

(71) Applicant: CHINESE ACADEMY OF MEDICAL SCIENCES INSTITUTE OF MEDICINAL PLANT DEVELOPMENT, Beijing (CN)

(72) Inventors: Xiaobo Sun, Beijing (CN); Yu Tian, Beijing (CN); Xiao Sun, Beijing (CN)

(73) Assignee: CHINESE ACADEMY OF MEDICAL SCIENCES INSTITUE OF MEDICINAL PLANT DEVELOPMENT, Beijing (CN)

( * ) Notice: Subject to any disclaimer, the term of this patent is extended or adjusted under 35 U.S.C. 154(b) by 0 days.

(21) Appl. No.: 18/271,036

(22) PCT Filed: Aug. 15, 2022

(86) PCT No.: PCT/CN2022/112512
§ 371 (c)(1),
(2) Date: Sep. 3, 2024

(87) PCT Pub. No.: WO2023/165094
PCT Pub. Date: Sep. 7, 2023

(65) Prior Publication Data
US 2025/0177342 A1    Jun. 5, 2025

(30) Foreign Application Priority Data
Mar. 4, 2022 (CN) .......................... 202210205661.2

(51) Int. Cl.
*A61K 31/24* (2006.01)
*A61K 31/235* (2006.01)
*A61P 9/10* (2006.01)
*C07C 68/00* (2020.01)
*C07C 69/76* (2006.01)
*C07C 205/59* (2006.01)

(52) U.S. Cl.
CPC ............ *A61K 31/24* (2013.01); *A61K 31/235* (2013.01); *A61P 9/10* (2018.01); *C07C 68/00* (2013.01); *C07C 69/76* (2013.01); *C07C 205/59* (2013.01)

(58) Field of Classification Search
CPC .. A61K 2300/00; A61K 31/235; A61K 31/24; A61K 45/06; A61P 13/12; A61P 25/00; A61P 25/28; A61P 27/02; A61P 3/10; A61P 9/00; A61P 9/10; C07C 205/59; C07C 2602/42; C07C 68/00; C07C 69/76
See application file for complete search history.

(56) References Cited

U.S. PATENT DOCUMENTS

| | | |
|---|---|---|
| 3,415,770 A | 12/1968 | Cunningham et al. |
| 5,389,643 A | 2/1995 | Miyazawa et al. |
| 2006/0166931 A1 | 7/2006 | Niu et al. |
| 2010/0076203 A1 | 3/2010 | Inagaki et al. |
| 2017/0044092 A1 | 2/2017 | Appendino et al. |

FOREIGN PATENT DOCUMENTS

| | | | | |
|---|---|---|---|---|
| CN | 1075145 A | 8/1993 | | |
| CN | 104224772 A | 12/2014 | | |
| CN | 106232570 A | 12/2016 | | |
| CN | 113402543 A | * 9/2021 | ........... | C07C 229/08 |
| CN | 114315585 A | 4/2022 | | |

OTHER PUBLICATIONS

Matsumura, A. et al., "Asymmetric electrochemical polymerization in cholesteric liquid crystalline media: Effect of isomeric structures of chiral inducers containing bornyl group," Synthetic Metals, vol. 22, pp. 157-164 (2015).
CN Office Action dated Apr. 19, 2022 as received in Application No. 202210205661.2.
International Search Report and Written Opinion of the International Searching Authority dated Nov. 25, 2022 as received in Application No. PCT/CN2022/112512.

* cited by examiner

*Primary Examiner* — Jean P Cornet
(74) *Attorney, Agent, or Firm* — Maschoff Brennan

(57) ABSTRACT

Disclosed are a hydroxypentyl benzoic acid diester compound, a method preparing the same, and an application of the same. This application uses a combination principle, on the one hand, the medicine concentration of butylphthalide in cerebral vessels is improved through a function of promoting the medicine to penetrate through a blood-brain barrier of dexborneol, and a multi-target multi-channel synergistic brain protection effect of the medicine is exerted; on the other hand, the treatment effect of dexborneol on cerebral ischemia is exerted. Anti-cerebral ischemia in-vivo pharmacodynamic activity evaluation is carried out on the synthesized compound, a high-activity candidate medicine is obtained, and industrial production can be achieved through the synthesis method.

20 Claims, 30 Drawing Sheets

HYDROXYPENTYL BENZOIC ACID DIESTER COMPOUND, AND PREPARATION METHOD AND PHARMACEUTICAL APPLICATION THEREOF

CROSS-REFERENCE TO RELATED APPLICATION

This application claims priority to Chinese patent application with application number 202210205661.2 filed on Mar. 4, 2022 to China National Intellectual Property Administration, entitled "Hydroxypentyl benzoic acid diester compound as well as preparation method and pharmaceutical application thereof", which is hereby incorporated by reference in its entirety.

FIELD OF THE INVENTION

The present invention relates to a new hydroxypentyl benzoic acid diester compound, specifically relates to a conjugate of a bimolecular dexborneol and 2-(α-hydroxy n-amyl) benzoic acid (i.e. ring-opening butylphthalide) and apreparation method and application thereof.

BACKGROUND OF THE INVENTION

Stroke is an acute cerebrovascular disease caused by cerebral ischemia and hypoxia, which is mainly divided into two categories: ischemic and hemorrhagic. Among them, ischemic stroke accounts for more than 70%, with a high incidence rate, mortality and disability rate, which seriously endangers human health and life. At present, there are two main methods of medicine treatment for ischemic stroke: one is to use thrombolysis, antiplatelet aggregation, anticoagulation, and anti-fibrinogen medicines, and the other is to use neuroprotective medicines to reduce nerve cell damage or apoptosis caused by ischemia. In recent years, intravascular thrombectomy has shown great value in the treatment of acute ischemic stroke. However, few stroke patients have access to this treatment, and less than half of them can benefit permanently. Tissue-type plasminogen activator alteplase is the only medicine approved by the FDA in US for the treatment of acute ischemic stroke, but its application is limited due to its narrow therapeutic window, easy to produce hemorrhagic adverse reactions and no neuroprotective activity, etc. Therefore, it is of great significance to develop a class of drugs that can improve the blood supply function of the brain and have some neuroprotective effects for the treatment of ischemic stroke.

3-n-nutylphthalide (NBP, hereinafter referred to as formula A) is a benzofuran ketone compound extracted from celery seeds, and its chemical name is (R/S)-3-n-butyl-1 (3H)-isobenzofuranone. NBP is a medicine independently developed in China and launched in 2002 for the treatment of ischemic stroke. In "China Guidelines for the Treatment of Acute Ischemic Stroke 2018", NBP is defined as a "medicine that improves cerebral blood circulation". NBP has various biological activities such as anti-platelet aggregation, anti-thrombosis, reducing cerebral infarction volume, improving cerebral microcirculation, etc. Although NBP can treat multiple pathological links of cerebral ischemia, its water solubility is extremely poor. In order to improve its water solubility and activity, the structure of NBP has been modified and reformed through chiral resolution, introduction of substituents on the benzene ring, ring-opening of lactone followed by derivatization, and other methods. 2-(α-hydroxy n-amyl) benzoic acid is a lactone ring-opening product of NBP, which has similar biological activity and pharmacokinetic characteristics to NBP. However, it is unstable both in vivo and in vitro, making it difficult to prepare medicines suitable for clinical application. Due to its limited therapeutic effect, NBP is often used in combination with other medicines in clinical practice to enhance its efficacy. For example, in CN107595874A, butylphthalide is used in combination with mecobalamine to increase the therapeutic effect of butylphthalide, thereby reducing the effective dose and dosage of butylphthalide, and reducing the occurrence of adverse reactions in long-term use.

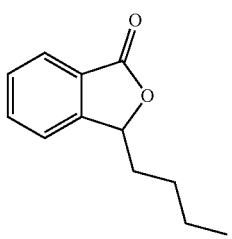

A: butylphthalide (NBP);

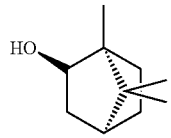

B: dexborneol ((+)-borneol)

Dexborneol, or dexhandrinol (Formula B above), is often extracted from fresh branches and leaves of Lauraceae plants. It is a bicyclic monoterpene compound, also known as (+)-borneol. It has the functions of awakening the brain and opening the origins, promoting medicines to penetrate the blood-brain barrier, protecting cardiovascular and cerebrovascular vessels, preventing thrombosis, analgesia and anti-inflammatory, and anti-bacteria, etc. Modern pharmacological research shows that borneol can increase the concentration of medicines in the cardiovascular and cerebrovascular systems and promote the opening of the blood-brain barrier by inhibiting the efflux of transporters, regulating the level of biochemical substances, changing the structure of the stratum corneum of the skin, and adjusting the structure of endothelial cell junction. Therefore, it is often used in combination with other medicines to significantly extend the retention time of effective medicines and improve the efficacy. For example, in CN105267212A, Edaravone and dexborneol are used in combination for treating cardio cerebral vascular disease. Patent application CN113402543A attempted to modify butylphthalide, but its modified new compound showed no significant improvement in efficacy compared to butylphthalide, and there was no statistical difference between the two effects, making it difficult to prepare medicines suitable for clinical application. In order to develop more medicines for the treatment of cardio cerebral vascular disease, the inventor team of this application has carried out a determined research.

SUMMARY OF THE INVENTION

Based on the effects of both butylphthalide and dexborneol on improving cerebral circulation and protecting cardio cerebral vessels, the inventor team of this application adopted progressive pre-experiments. First, butylphthalide and dexborneol were simply combined in a molar ratio 1:1 to form a composition. It was found that when the composition was administered by injection in vivo or oral administration, compared with butylphthalide or dexborneol alone, the effect of reducing the cerebral infarction area in rats with middle cerebral artery occlusion (MCAO) model is not significant. On this basis, we explored the formation of a new compound (as shown in the following formula B) by conjugating the ring-opening product of butylphthalide with dexborneol in a molar ratio of 1:1, and found that the activity of the compound was only slightly improved. Furthermore, we conjugated the ring-opening product of butylphthalide with dexborneol in a molar ratio of 1:2 and found that the activity of 2-(α-hydroxy n-amyl) benzoic acid derivatives (as shown in the following formula C) substituted with two molecules of dexborneol is significantly better than that of 2-(α-hydroxy n-amyl) benzoic acid derivatives (as shown in the following formula B) substituted with one molecule of dexborneol. In addition, this application further investigated the effect of chiral configuration on activity and found that in the same 2-(α-hydroxy n-amyl) benzoic acid derivatives substituted with two molecules of dexborneol, the activity of the levorotatory compound (as shown in he following formula D) is superior.

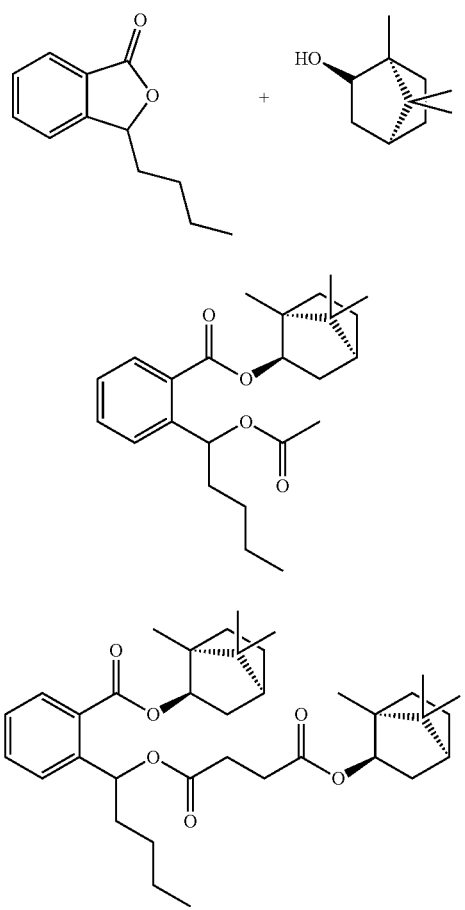

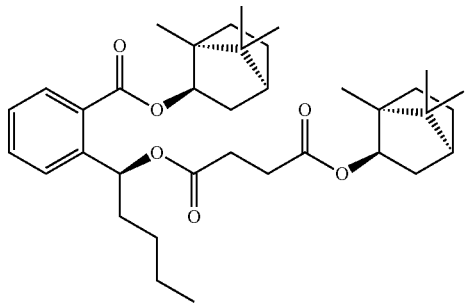

A: butylphthalide and dexborneol composition (1:1); B: butylphthalide and dexborneol conjugate (1:1); C: butylphthalide and dexborneol conjugate (1:2); D: Levobutylphthalide and dexborneol conjugate (1:1)

In this application, a series of 2-(α-hydroxy n-amyl) benzoic acid derivatives substituted with two molecule dexborneol are obtained by conjugating the ring-opening product of butylphthalide or levobutylphthalide with dexborneol in a specific ratio. The derivatives improve the medicine concentration of butylphthalide ring-opening products in the cerebral vessels by promoting the medicine to penetrate through the blood-brain barrier through dexborneol, and can play a multi-target multi-channel synergistic brain protection effect of the conjugating medicines. In this application, highly active clinical candidate medicines are obtained by evaluating the activity of cerebral infarction area in MCAO/R model rats with in vivo pharmacodynamics against cerebral ischemia, and the synthesis method can achieve industrial production. In this application, a series of hydroxypentyl benzoic acid diester compounds are obtained by conjugating the lactone ring-opening product of butylphthalide with bimolecular dexborneols, achieving structural optimization of butylphthalide and significantly improving its anti-ischemic effect.

The hydroxypentyl benzoic acid diester compound in this application has positive therapeutic value in clinical practice, and has obvious pharmacological properties, which is worth further development.

The general structural formula of the hydroxypentyl benzoic acid diester compound in this application is as follows:

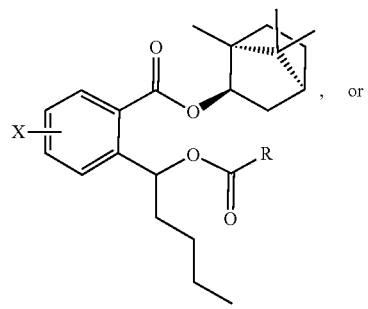

-continued
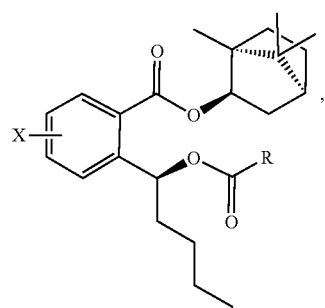
wherein R is
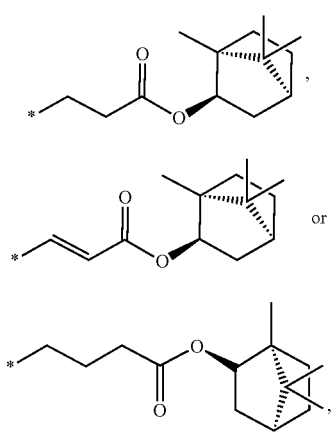
and
X is H, nitro, amino, F, Cl, Br, or I.
This application also provides a synthesis method for the above compounds.
Route 1:
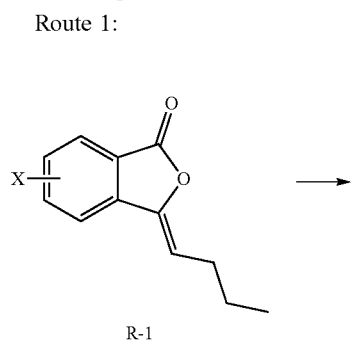
R-1
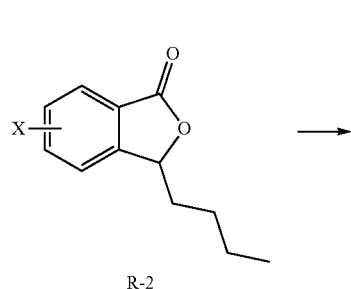
R-2
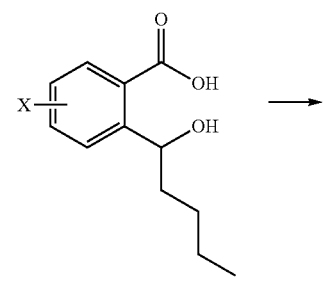
R-3
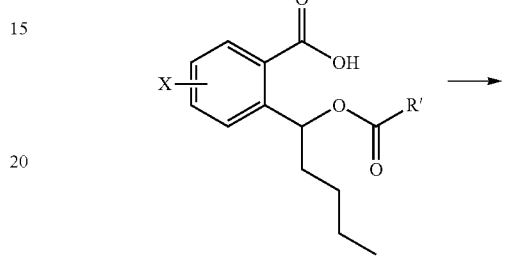
R-4
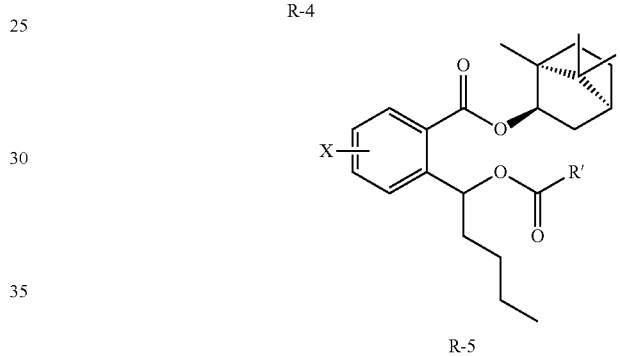
R-5
Route 2:
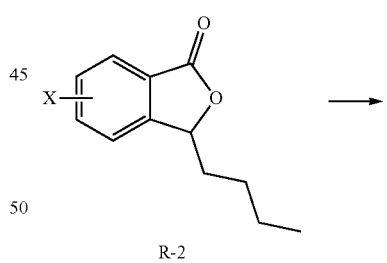
R-2
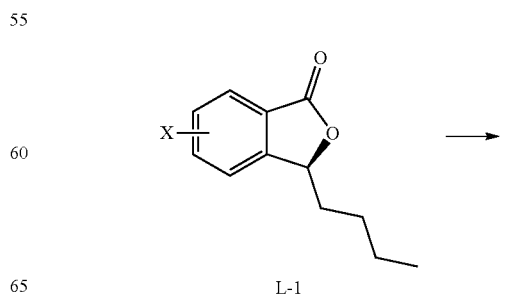
L-1

-continued

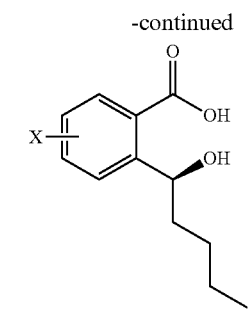

L-2

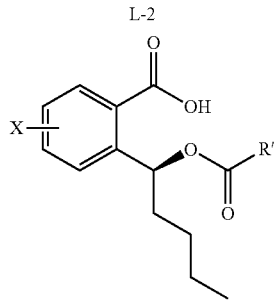

L-3

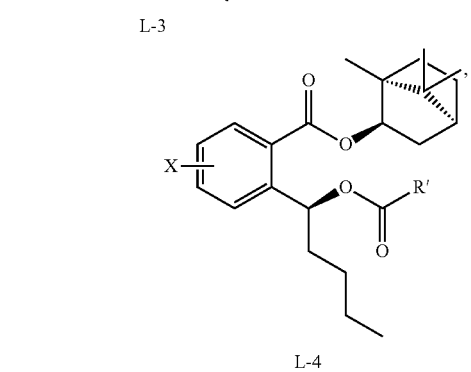

L-4 wherein R' is

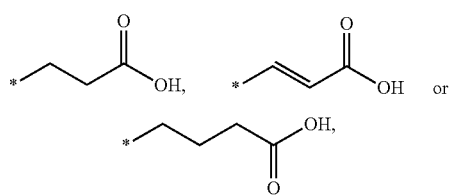

R is

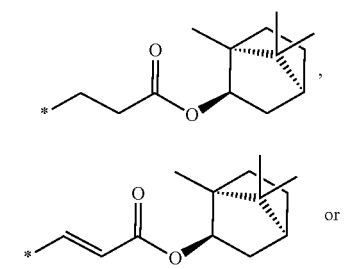

-continued

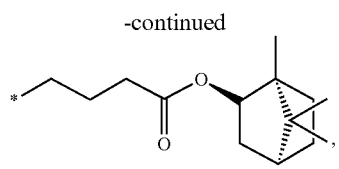

and

X is H, nitro, amino, F, Cl, Br, or I.

Route 1 comprises the following steps:
a). carrying out catalytic hydrogenation (palladium carbon, Raney nickel, etc.) on butenylphthalide or substituted butenylphthalide (R-1) to reduce a double bond to obtain butylphthalide or substituted butylphthalide racemate (R-2);
b). hydrolyzing R-2 with strong alkali (a molar ratio of sodium hydroxide, potassium hydroxide, etc. to R-2 is 5:1 to 1:1) under the reaction conditions selected from 1) or 2): 1) heating for reaction at a temperature of 20° C. to 120° C. for 1 hour to 5 hours; 2) carrying out microwave reaction at a temperature of 20° C. to 60° C. for 30 minutes to 1 hour; adjusting the pH to 2-4 with dilute acid after the reaction is completed, extracting with ethyl acetate, diethyl ether, etc., and concentrating to obtain an intermediate R-3; mixing R-3 sequentially with succinic anhydride (a molar ratio of succinic anhydride to R-2 is 5:1 to 1:1), DMAP, and Et$_3$N (a molar ratio of Et$_3$N to R-2 is 5:1 to 1:1) to obtain R-4;
c). performing a condensation reaction of R-4 with dexborneol (a molar ratio of dexborneol to R-4 is 10:1 to 2:1) catalyzed by DCC (a molar ratio of DCC to R-4 is 10:1 to 2:1) to obtain the target product R-5;

Route 2 comprises chemical chiral resolution on compound R-2 to obtain chiral compound L-1, followed by the above steps b) and c) to obtain the target product L-4.

The structures of the optional compounds of this application are as follows:

Compound 1

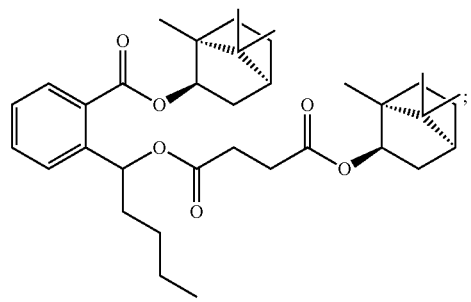

Compound 2

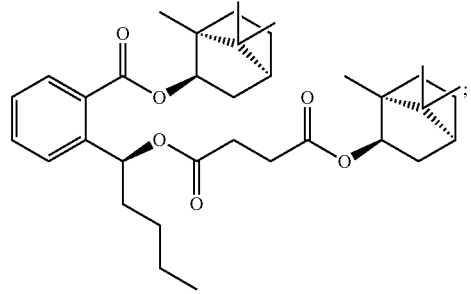

Compound 3
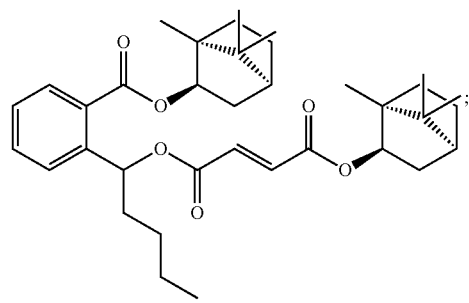
Compound 4
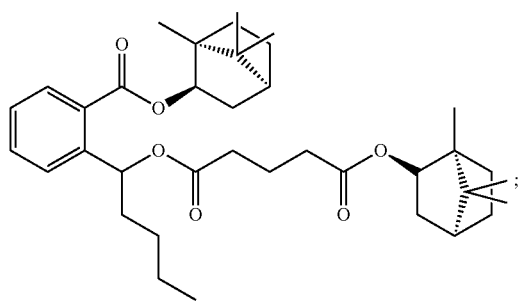
Compound 5
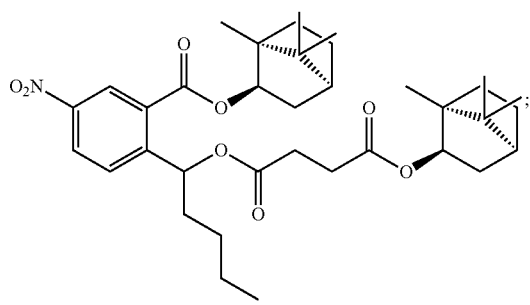
Compound 6
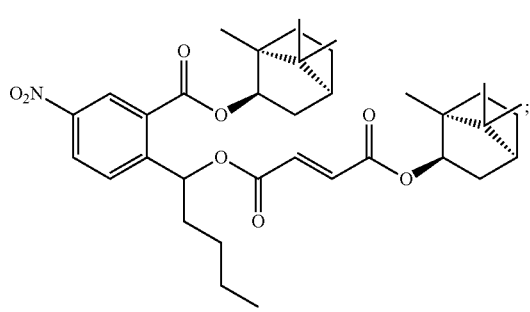
Compound 7
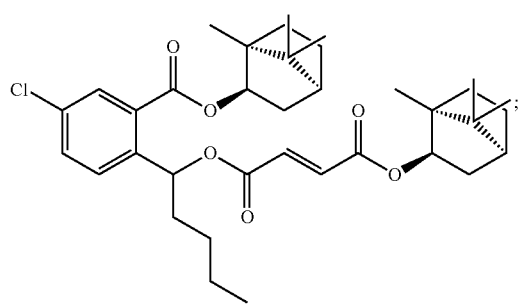
Compound 8
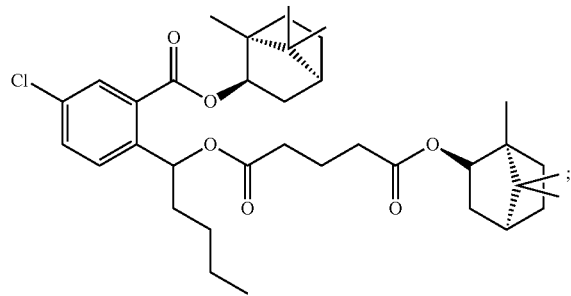
Compound 9
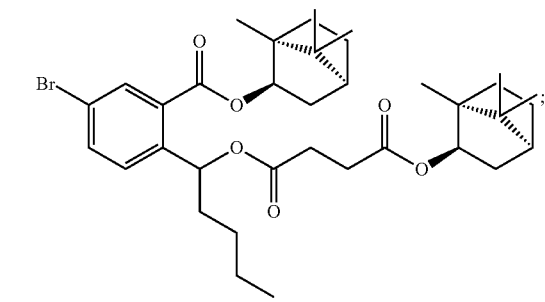
Compound 10
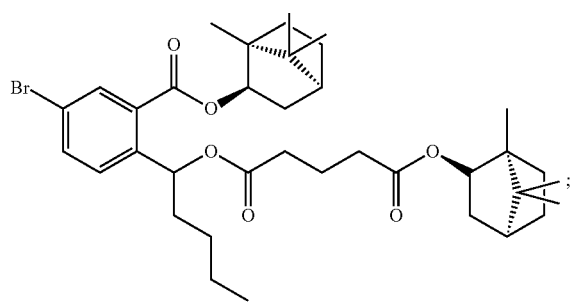
Compound 11
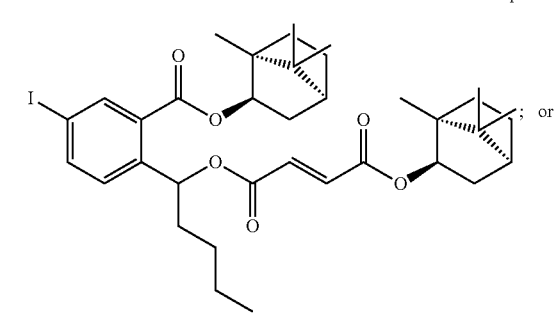
; or
Compound 12
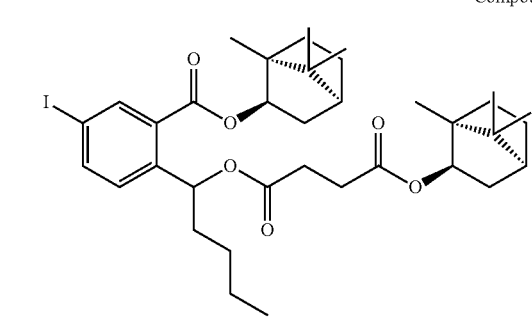

According to one aspect of the invention, a method for treating cardio cerebral vascular disease or vascular diseases induced by senile dementia or diabetes is provided, comprising administering a subject in need a therapeutic effective amount of the above compound or its composition or its preparation.

Optionally, the cardio cerebral vascular disease is an ischemic cardio cerebral vascular disease; the vascular diseases induced by diabetes are diabetes encephalopathy, diabetes heart disease, diabetic retinopathy or diabetes nephropathy.

Optionally, the ischemic cardio cerebral vascular disease is a cerebral infarction or myocardial infarction.

Optionally, the therapeutic effective amount is 7.5 mg/kg to 15 mg/kg.

DETAILED DESCRIPTION OF THE INVENTION

Preparation of Intermediate R-2

Figure 1:
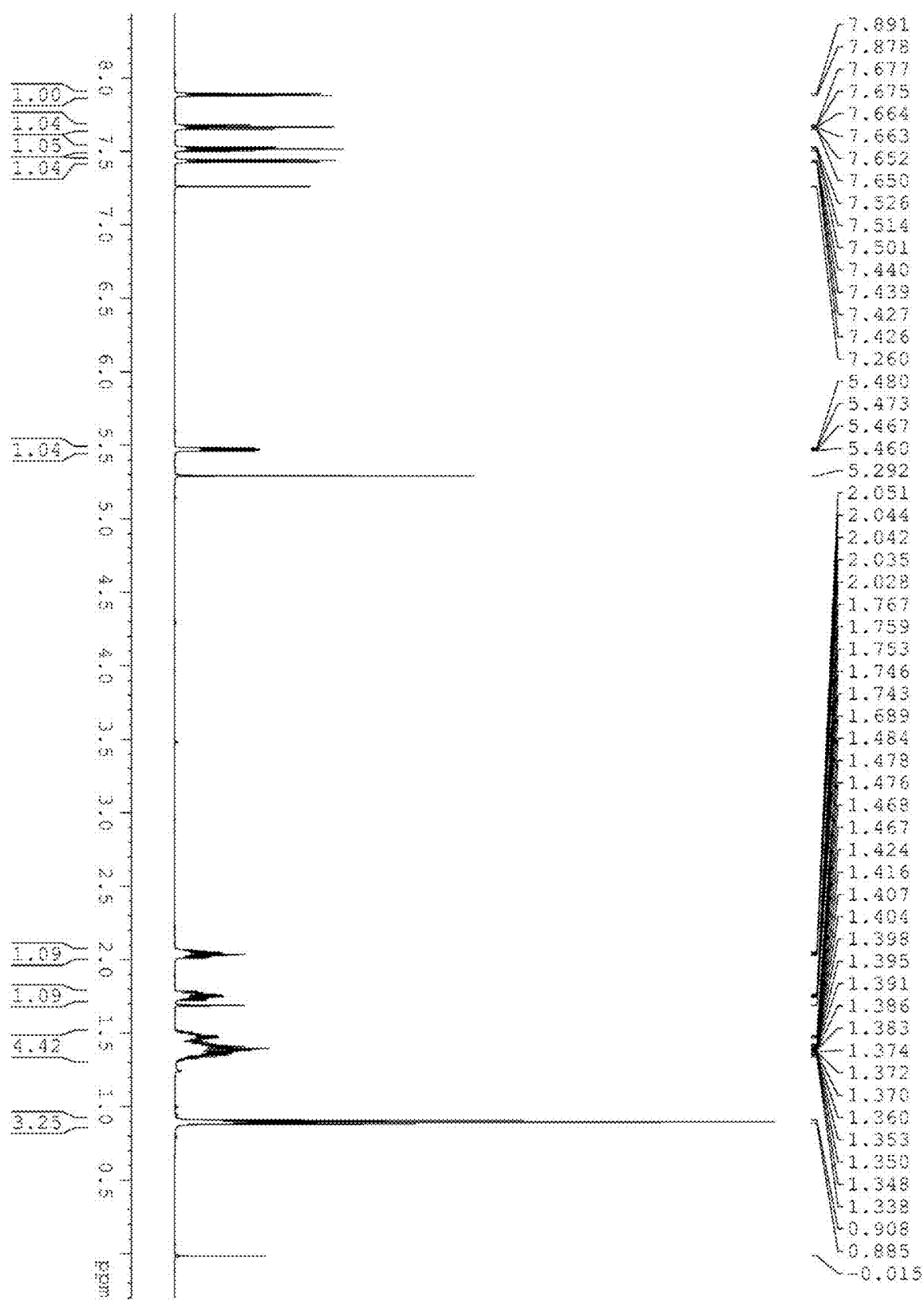
FIG. 1 is a $^1$H-NMR spectrum of intermediate R-2.
Figure 2:
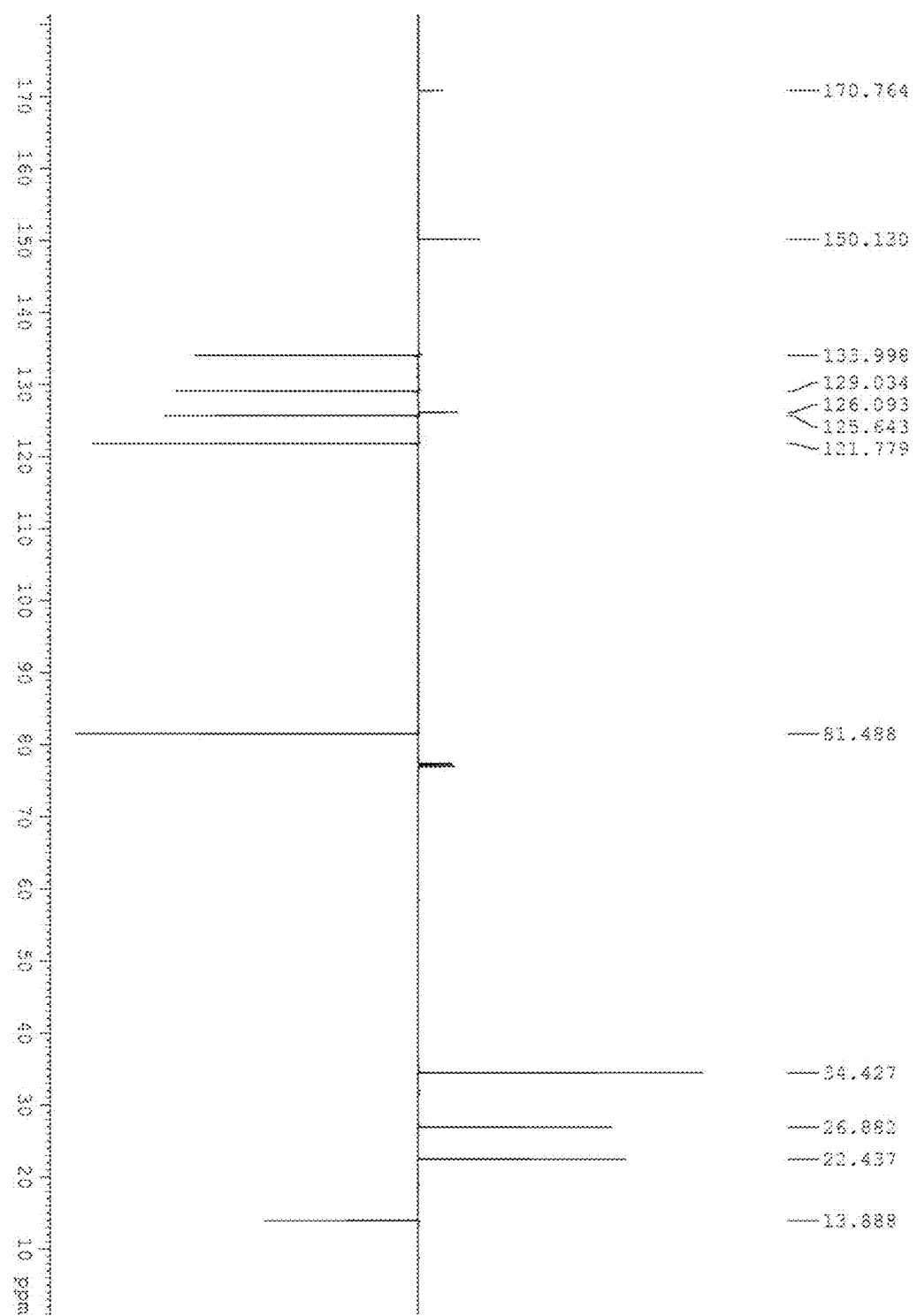
FIG. 2 is a $^{13}$C-APT spectrum of intermediate R-2.
Figure 3:
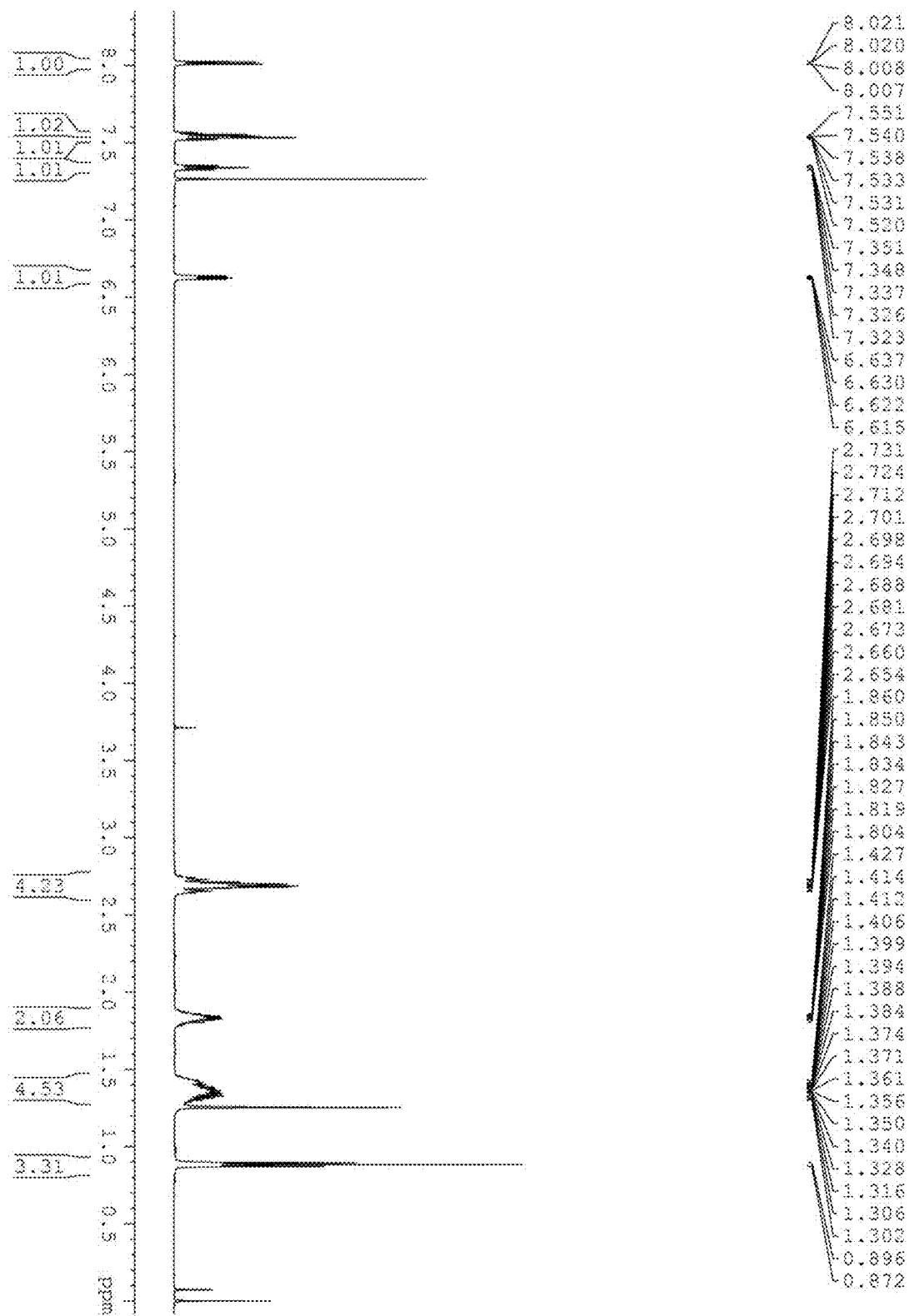
FIG. 3 is a $^1$H-NMR spectrum of intermediate R-4.
Figure 4:
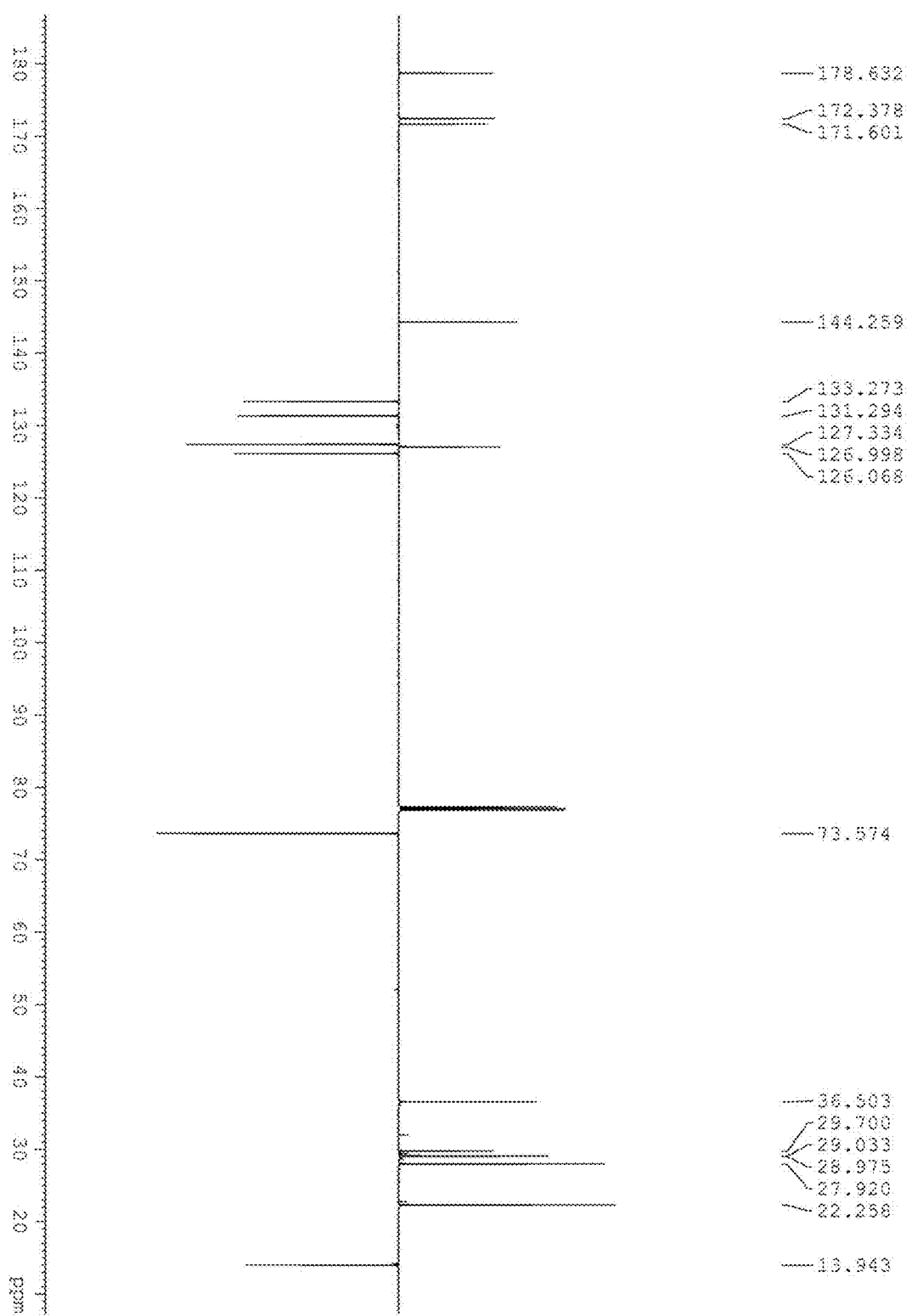
FIG. 4 is a $^{13}$C-APT spectrum of intermediate R-4.
Figure 5:
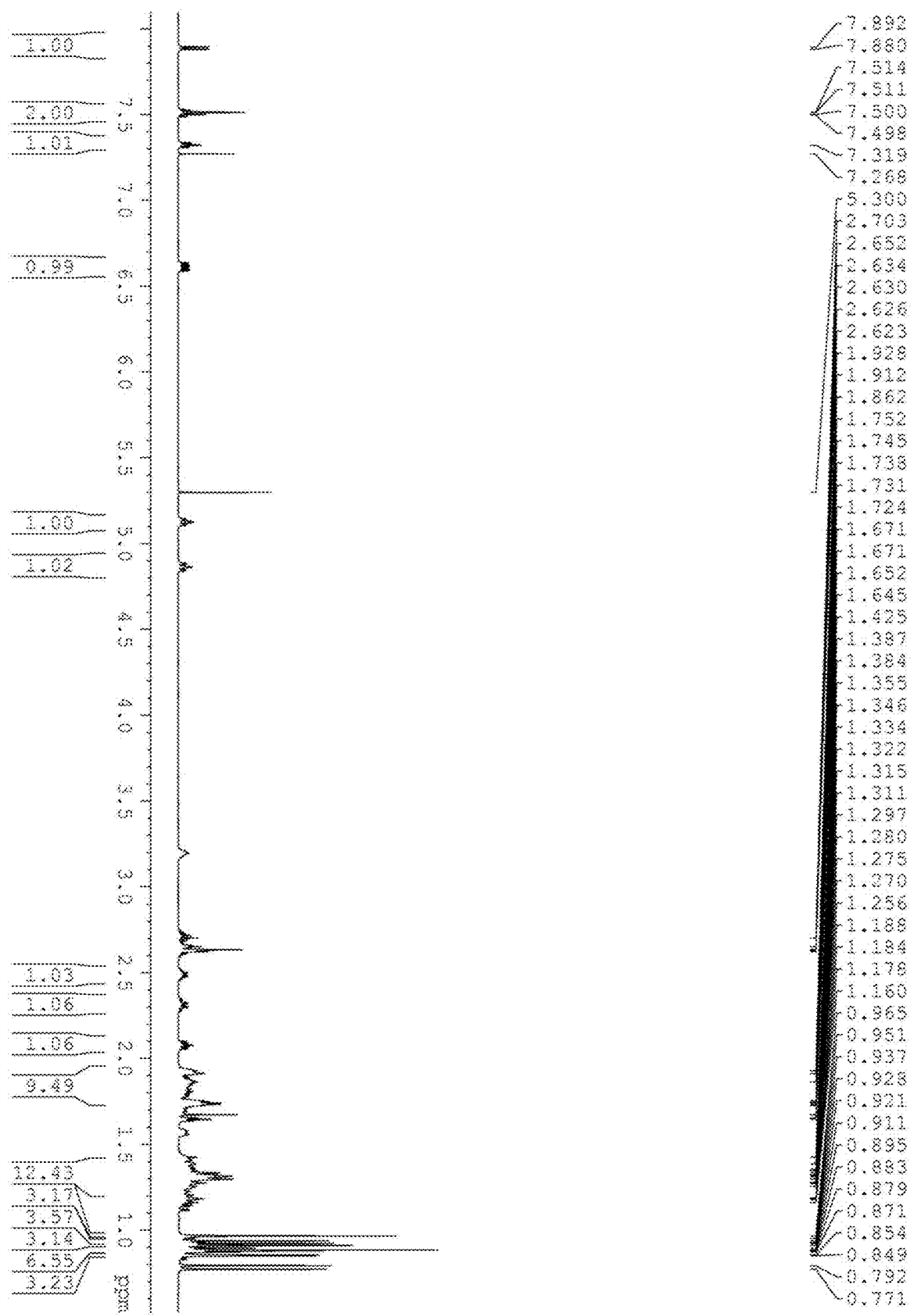
FIG. 5 is a $^1$H-NMR spectrum of compound 1 in Example 1.
Figure 6:
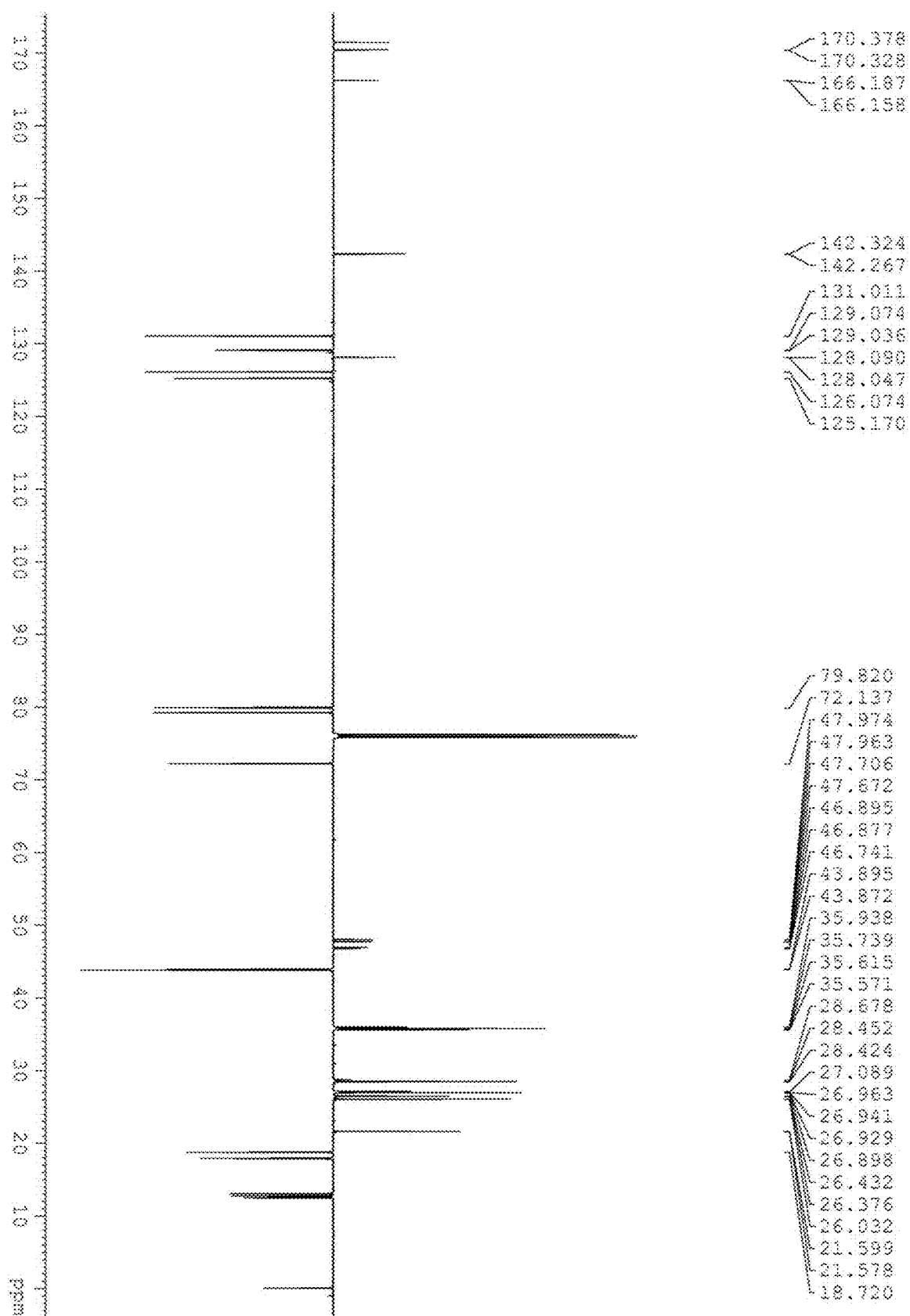
FIG. 6 is a $^{13}$C-APT spectrum of compound 1 in Example 1.
Figure 7:
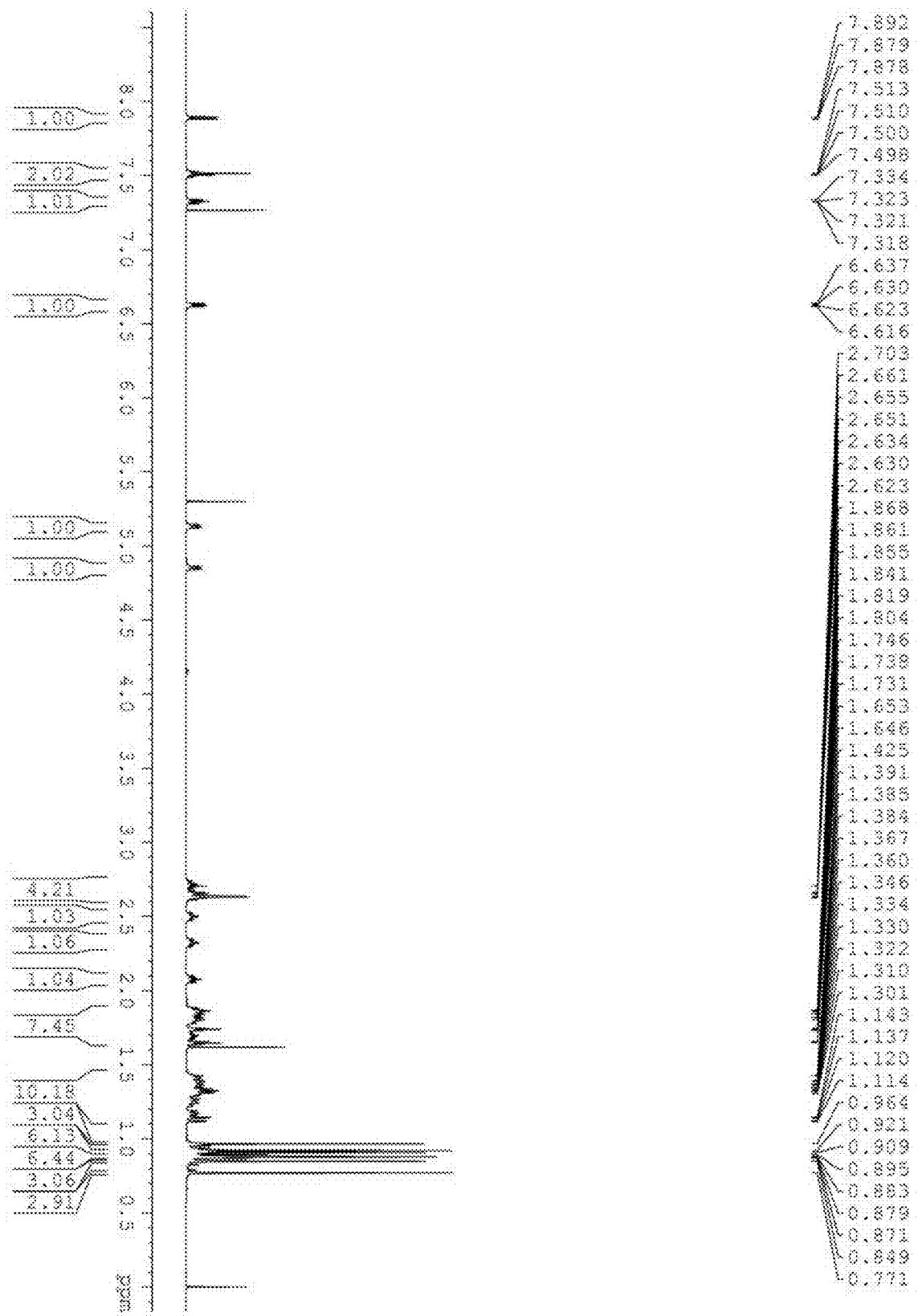
FIG. 7 is a $^1$H-NMR spectrum of compound 2 in Example 2.
Figure 8:
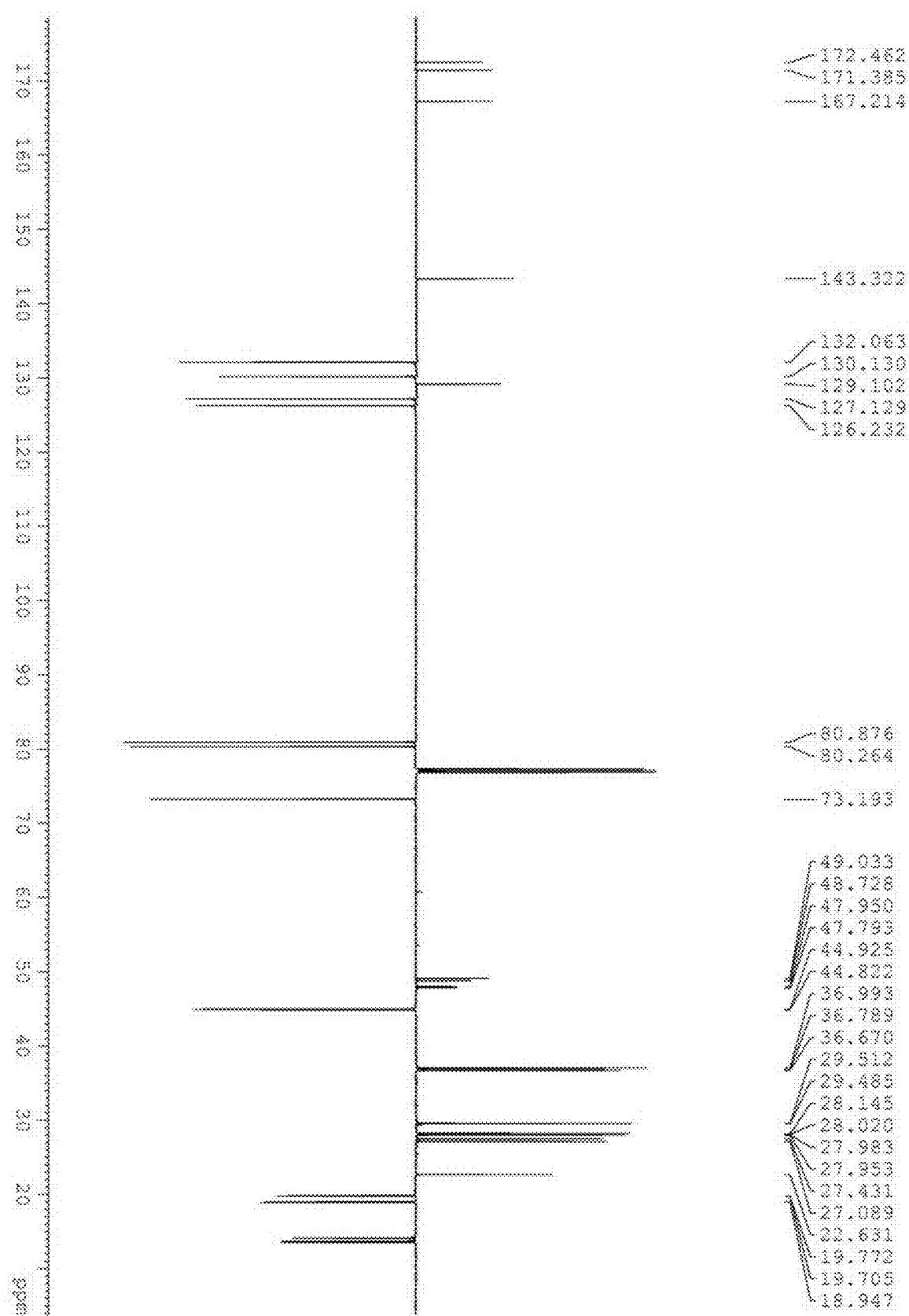
FIG. 8 is a $^{13}$C-APT spectrum of compound 2 in Example 2.
Figure 9:
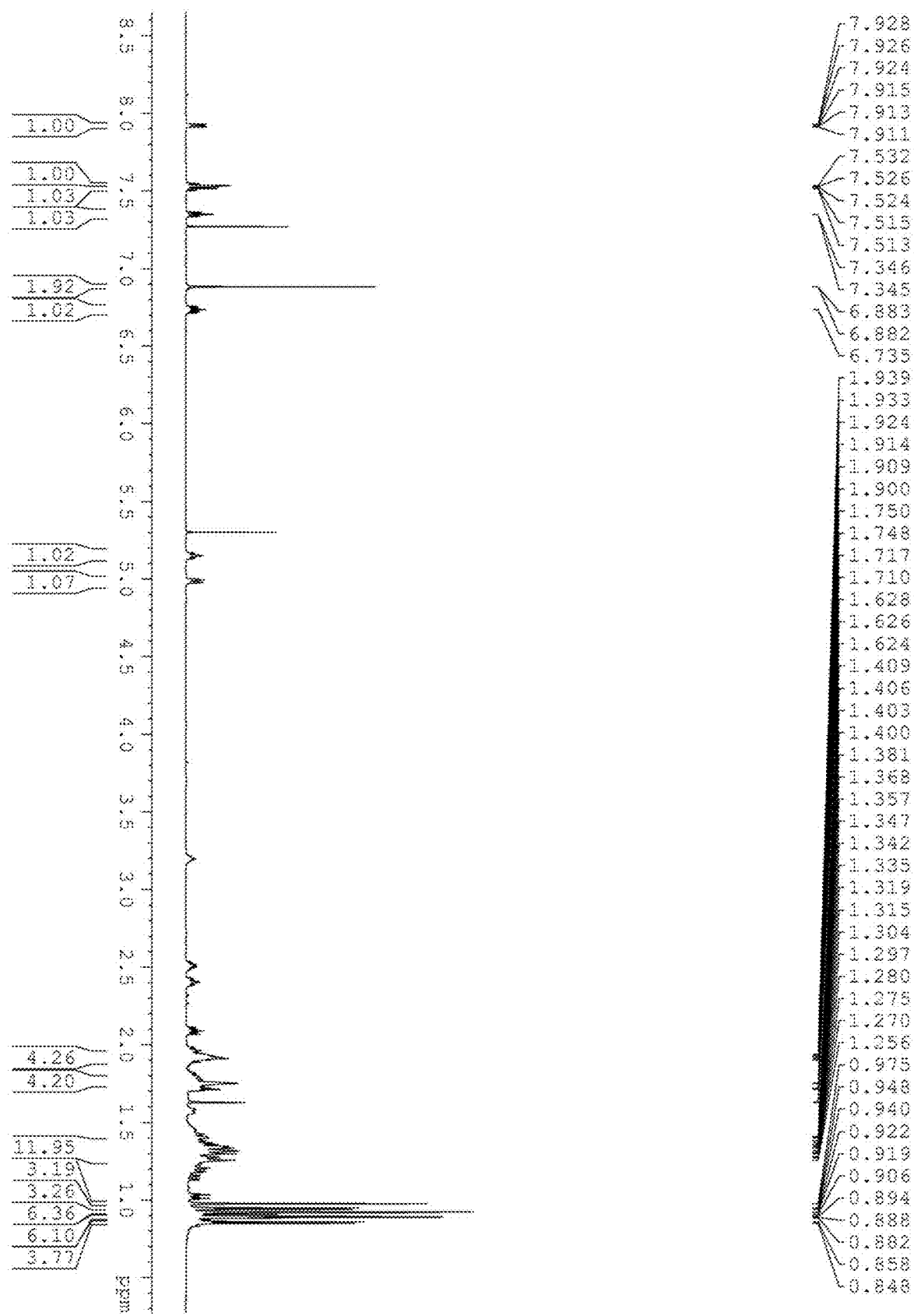
FIG. 9 is a $^1$H-NMR spectrum of compound 3 in Example 3.
Figure 10:
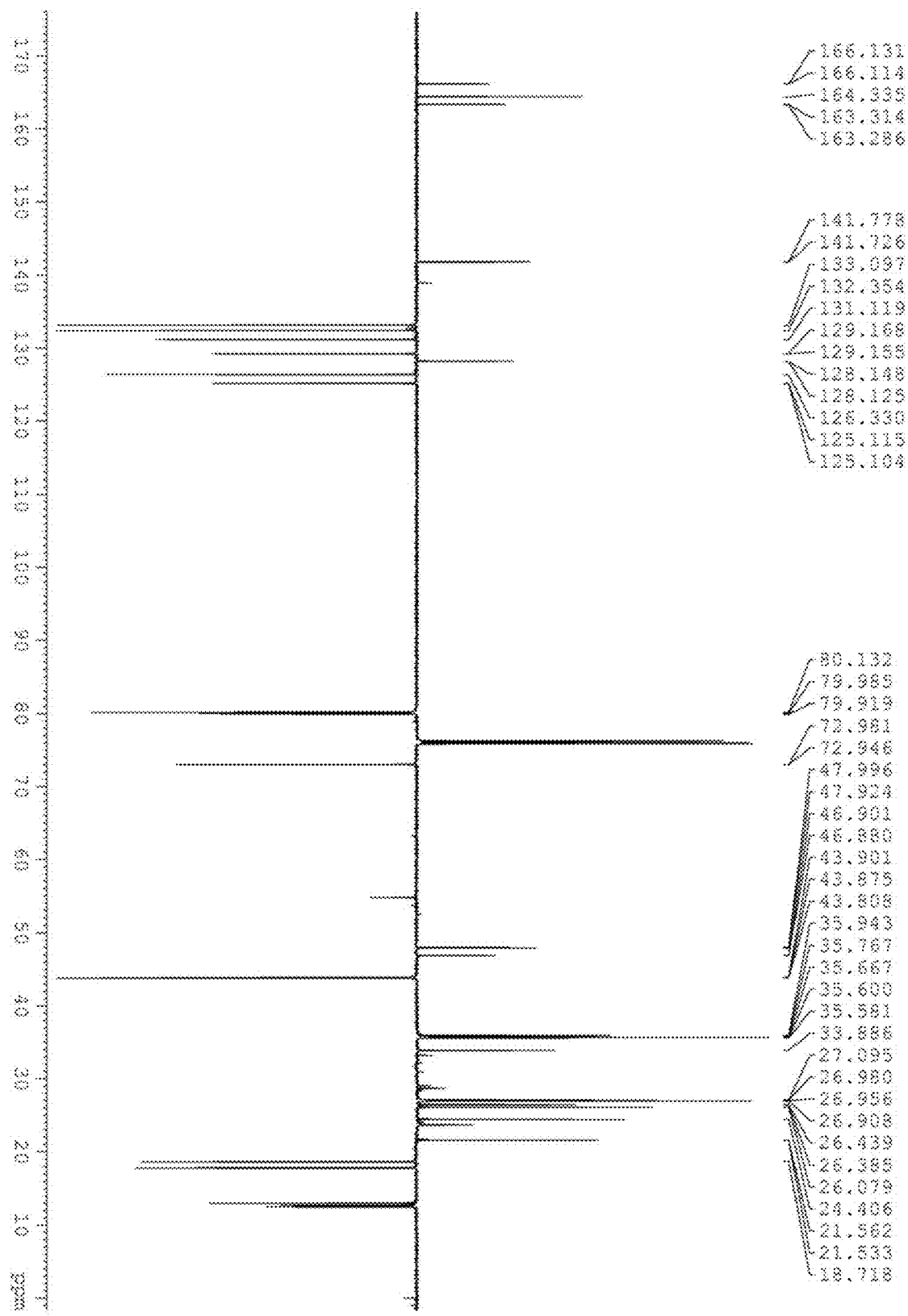
FIG. 10 is a $^{13}$C-APT spectrum of compound 3 in Example 3.
Figure 11:
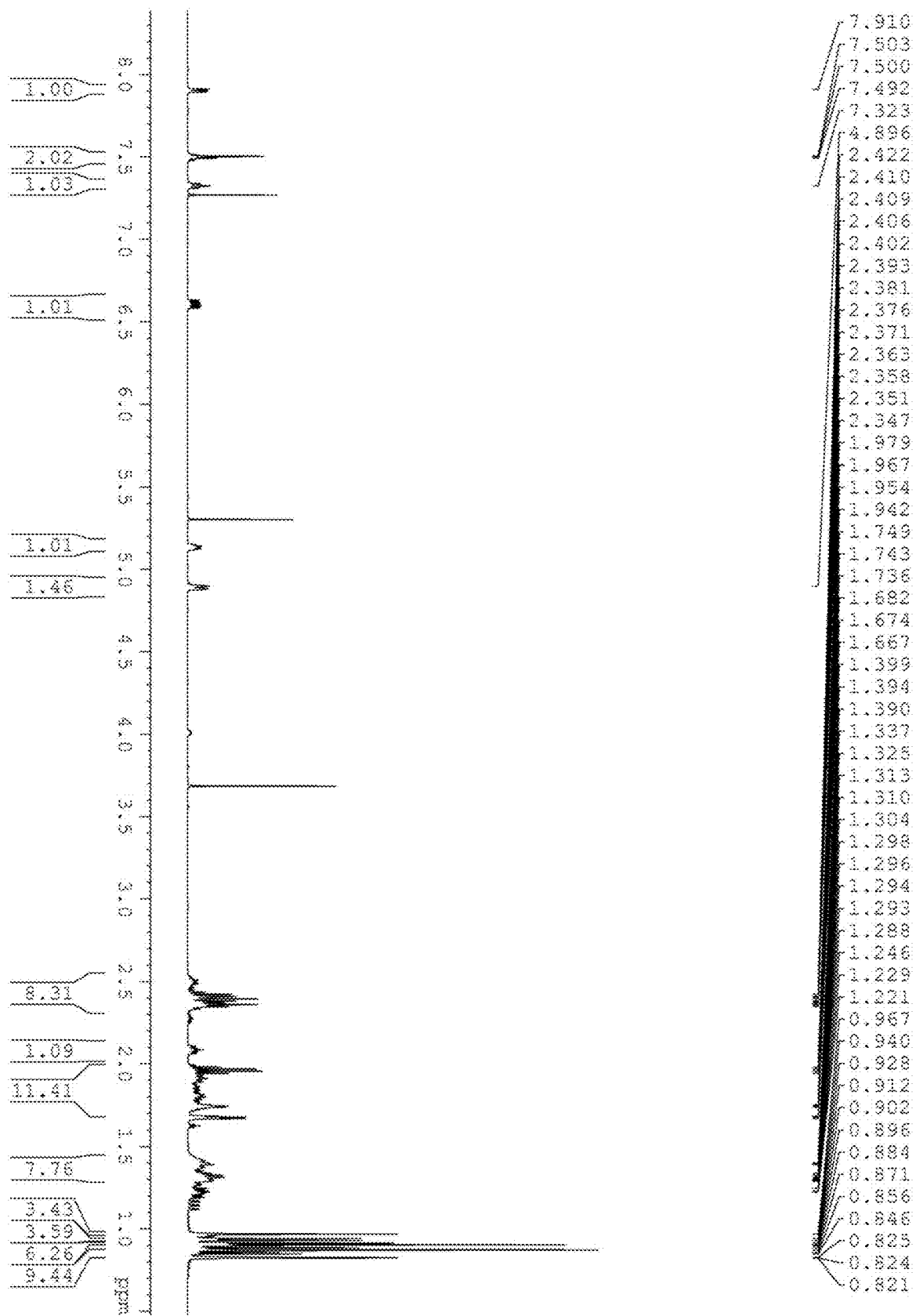
FIG. 11 is a $^1$H-NMR spectrum of compound 4 in Example 4.
Figure 12:
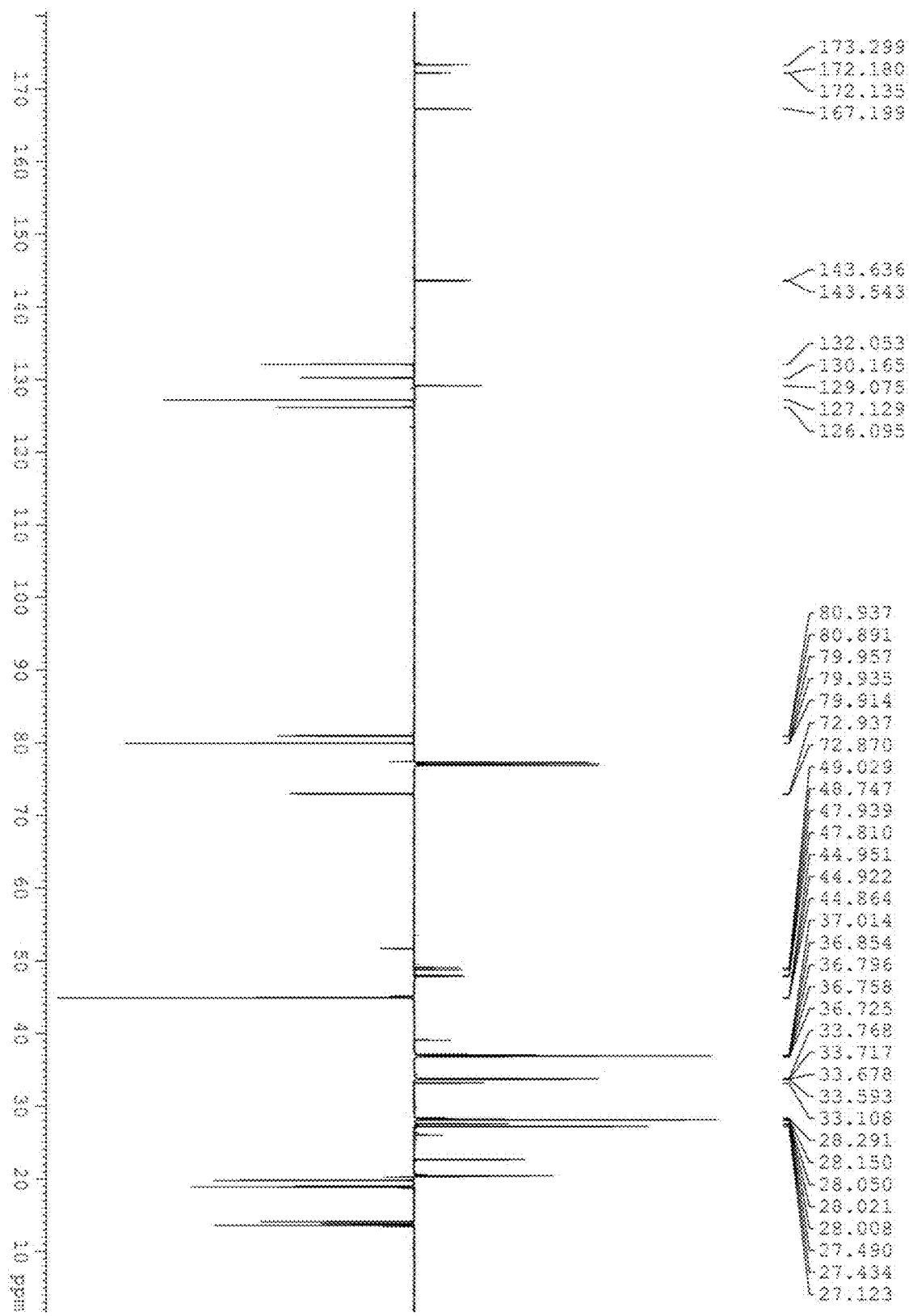
FIG. 12 is a $^{13}$C-APT spectrum of compound 4 in Example 4.
Figure 13:
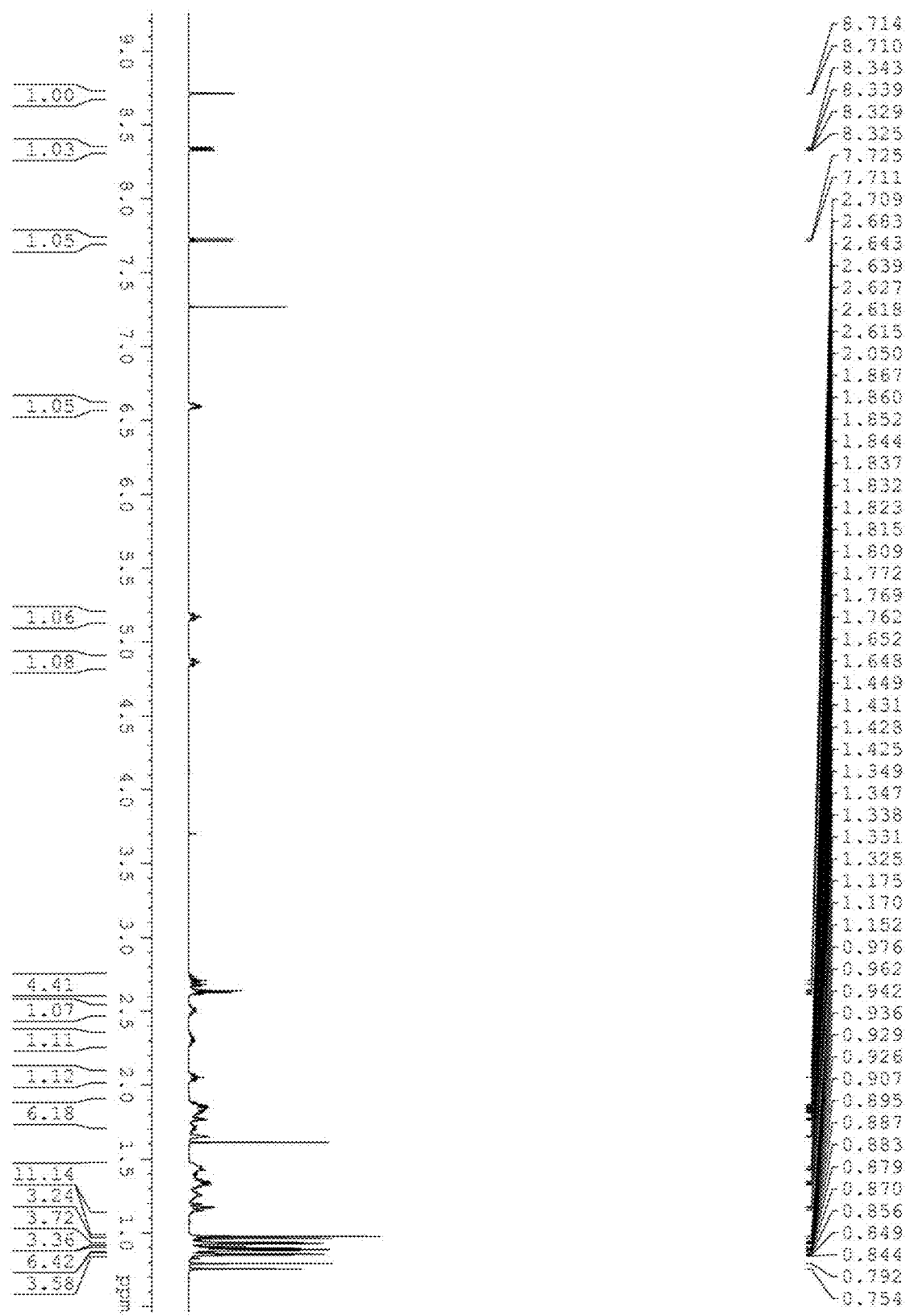
FIG. 13 is a $^1$H-NMR spectrum of compound 5 in Example 5.
Figure 14:
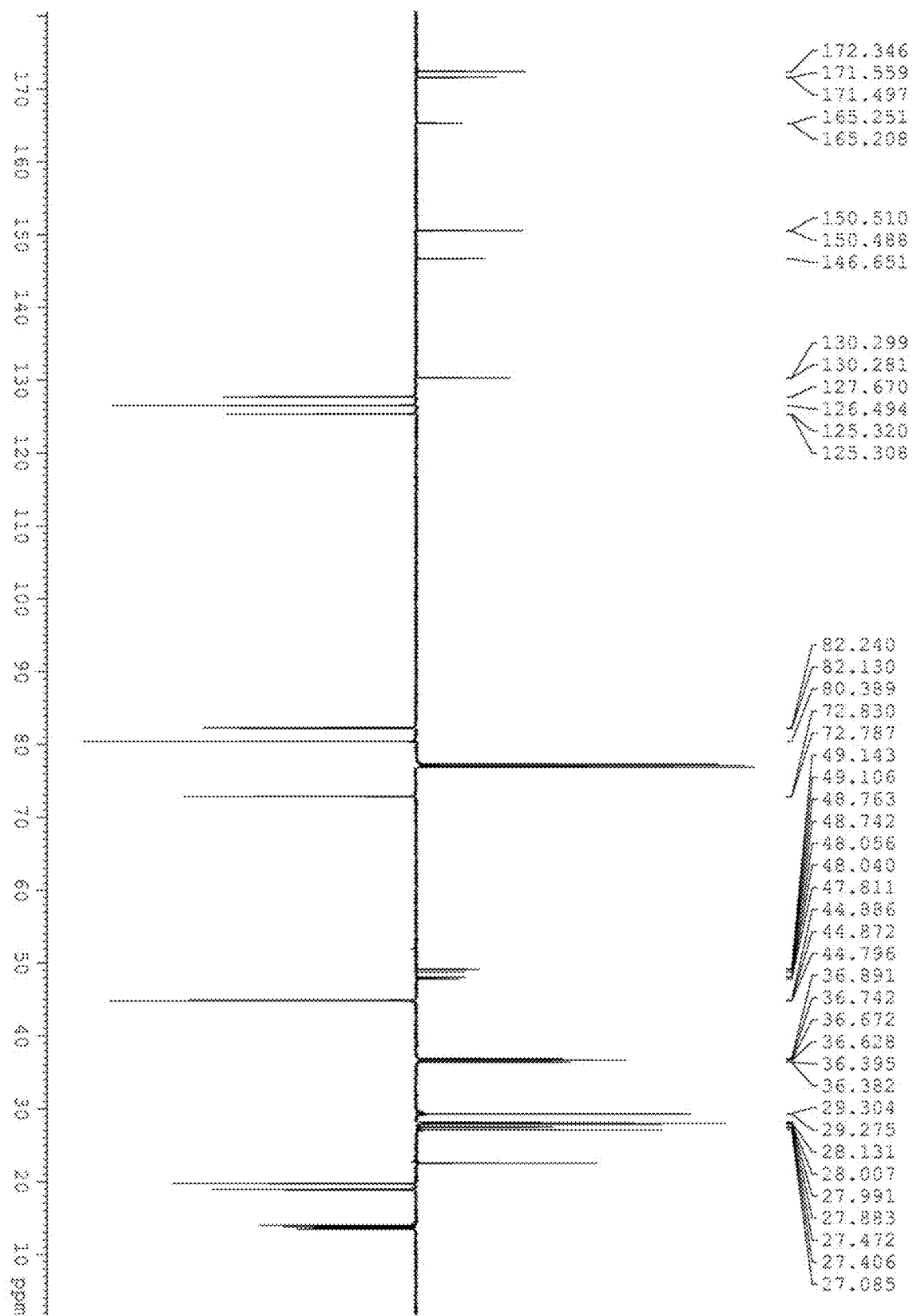
FIG. 14 is a $^{13}$C-APT spectrum of compound 5 in Example 5.
Figure 15:
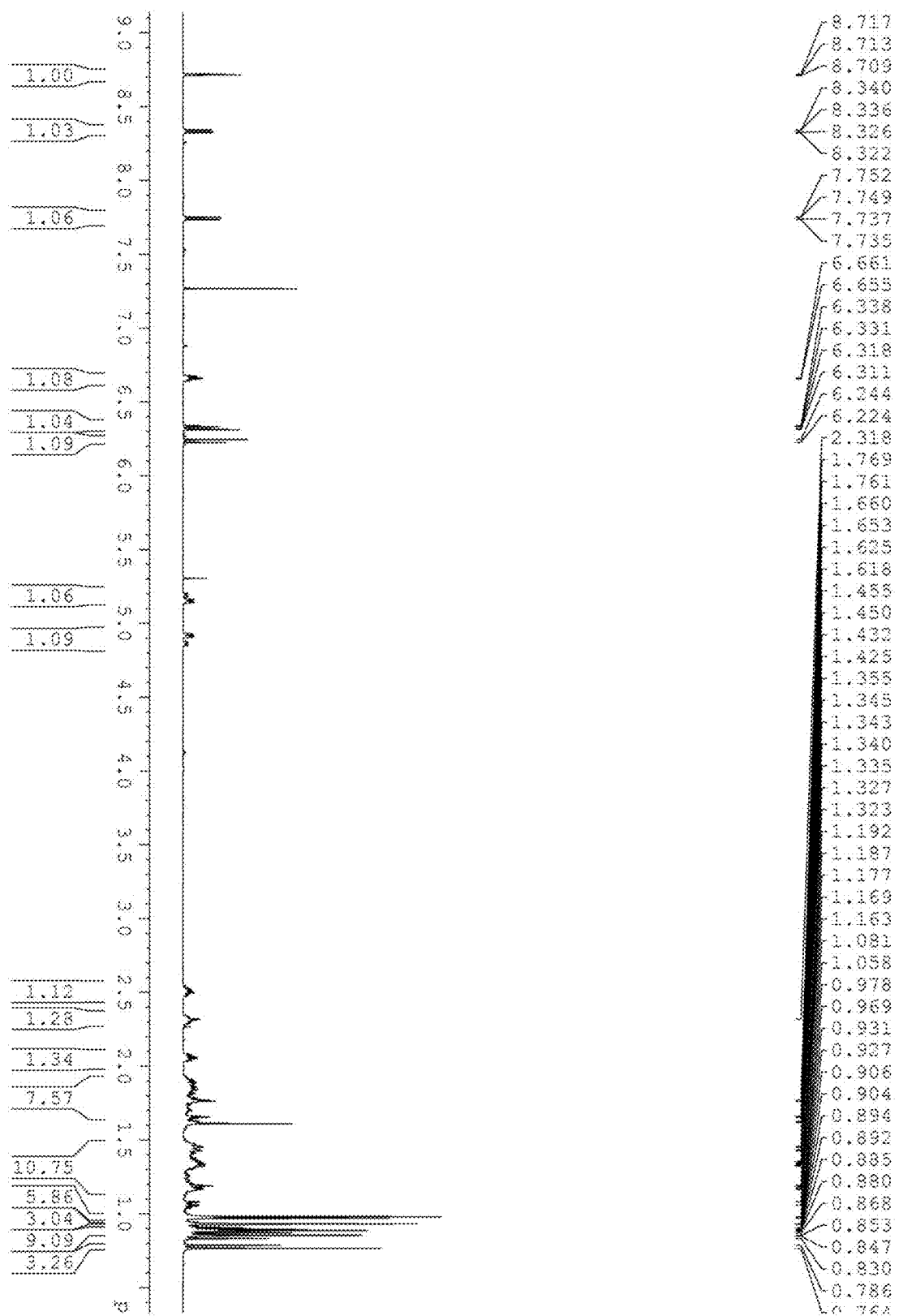
FIG. 15 is a $^1$H-NMR spectrum of compound 6 in Example 6.
Figure 16:
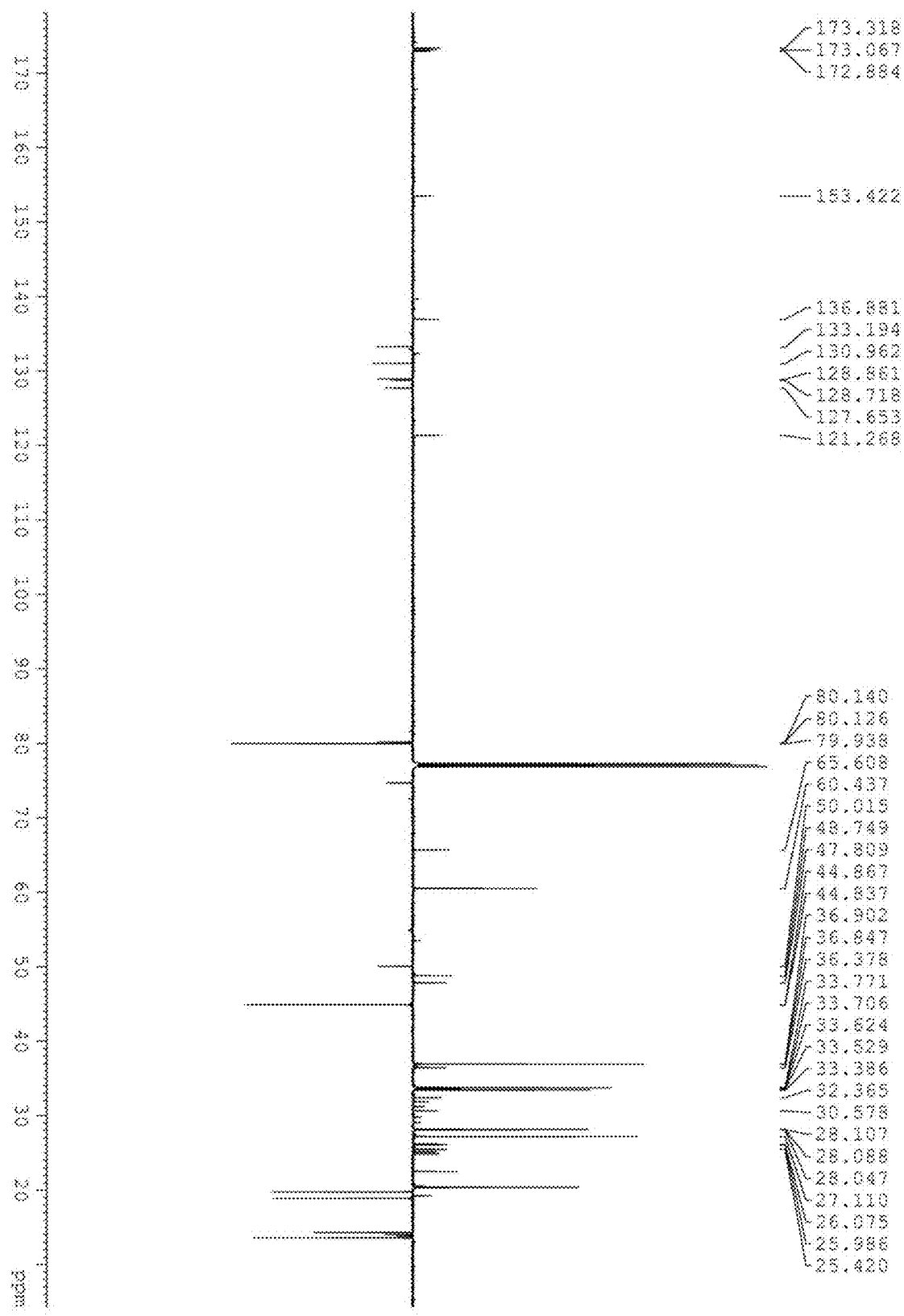
FIG. 16 is a $^{13}$C-APT spectrum of compound 6 in Example 6.
Figure 17:
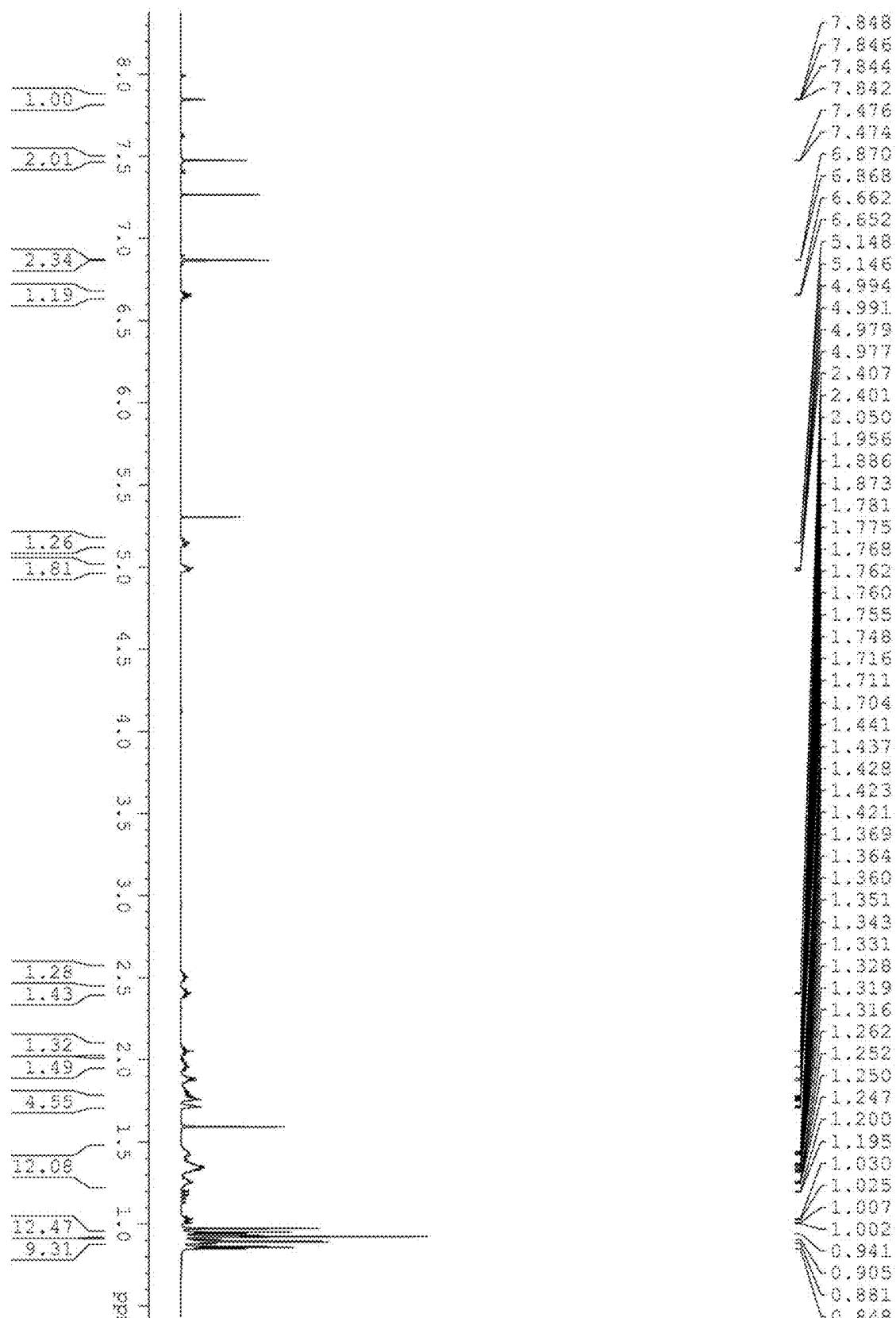
FIG. 17 is a $^1$H-NMR spectrum of compound 7 in Example 7.
Figure 18:
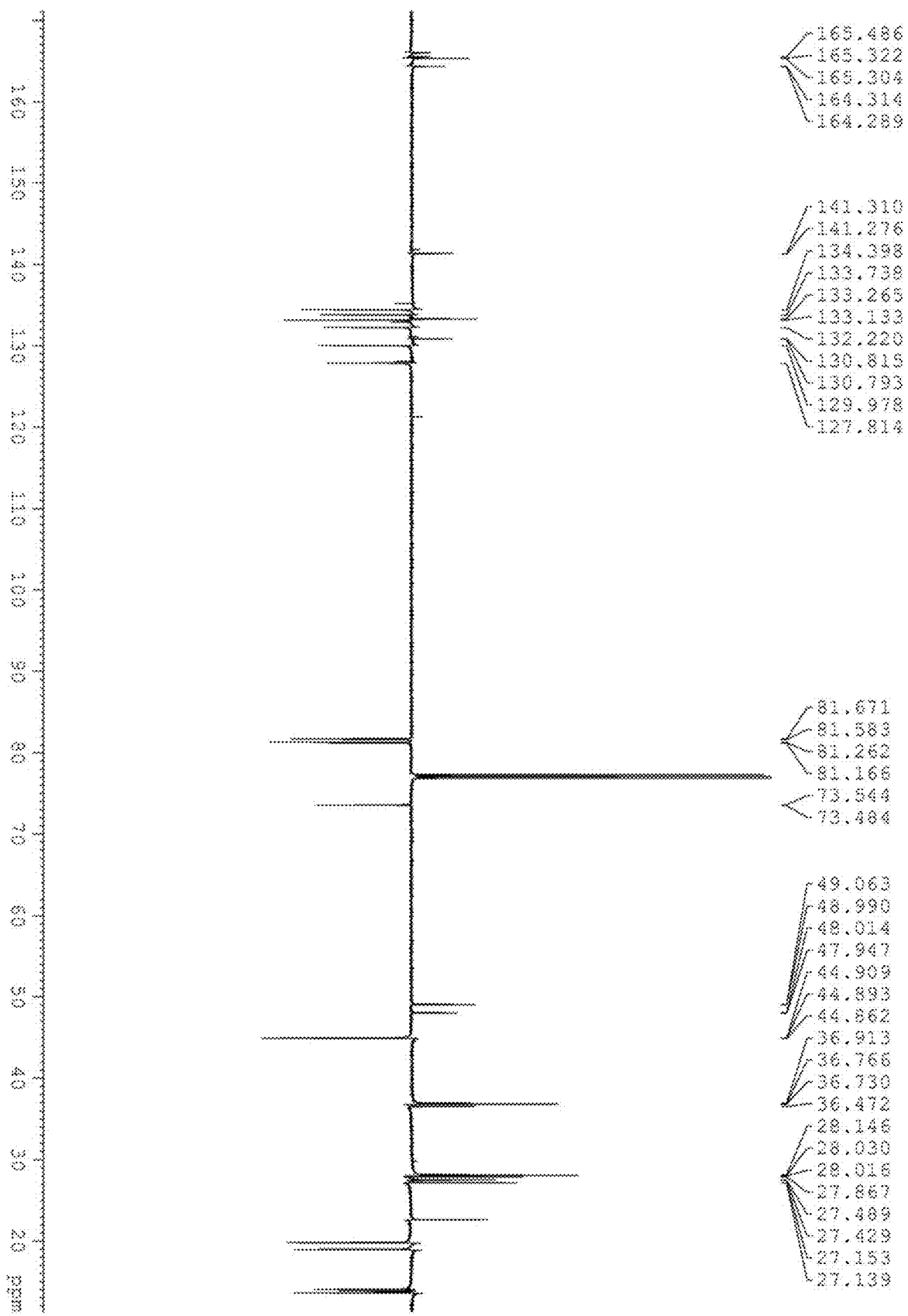
FIG. 18 is a $^{13}$C-APT spectrum of compound 7 in Example 7.
Figure 19:
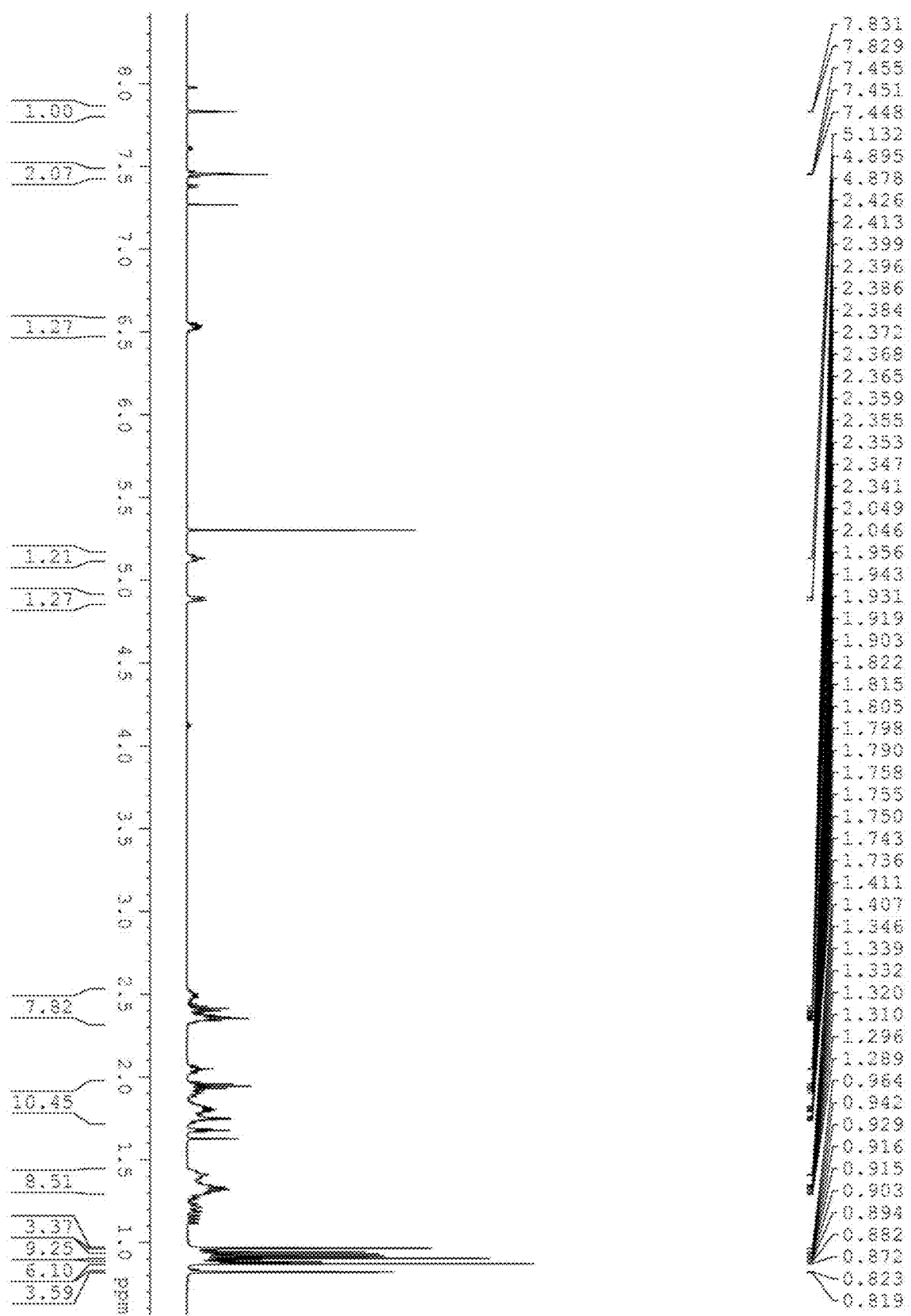
FIG. 19 is a $^1$H-NMR spectrum of compound 8 in Example 8.
Figure 20:
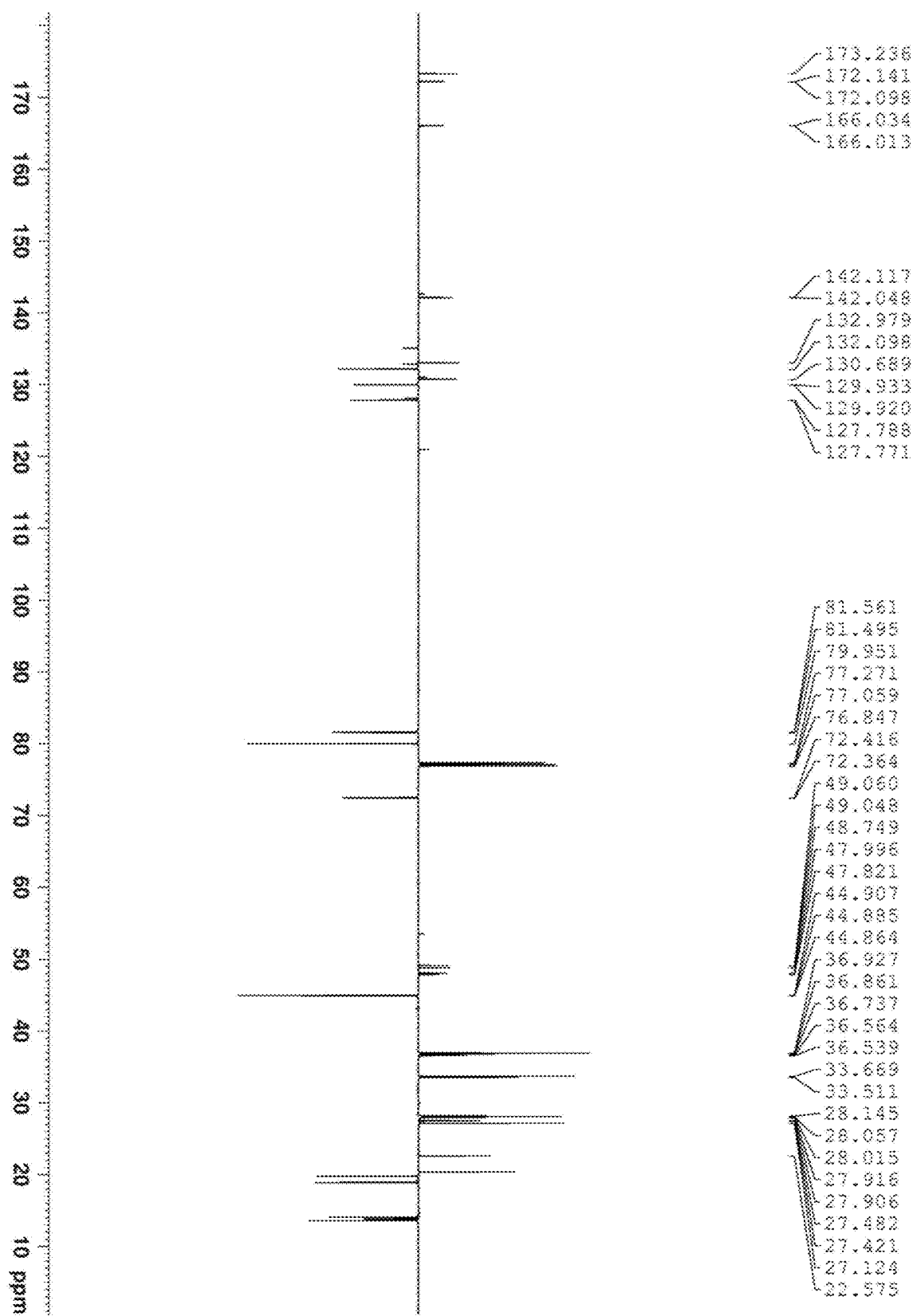
FIG. 20 is a $^{13}$C-APT spectrum of compound 8 in Example 8.
Figure 21:
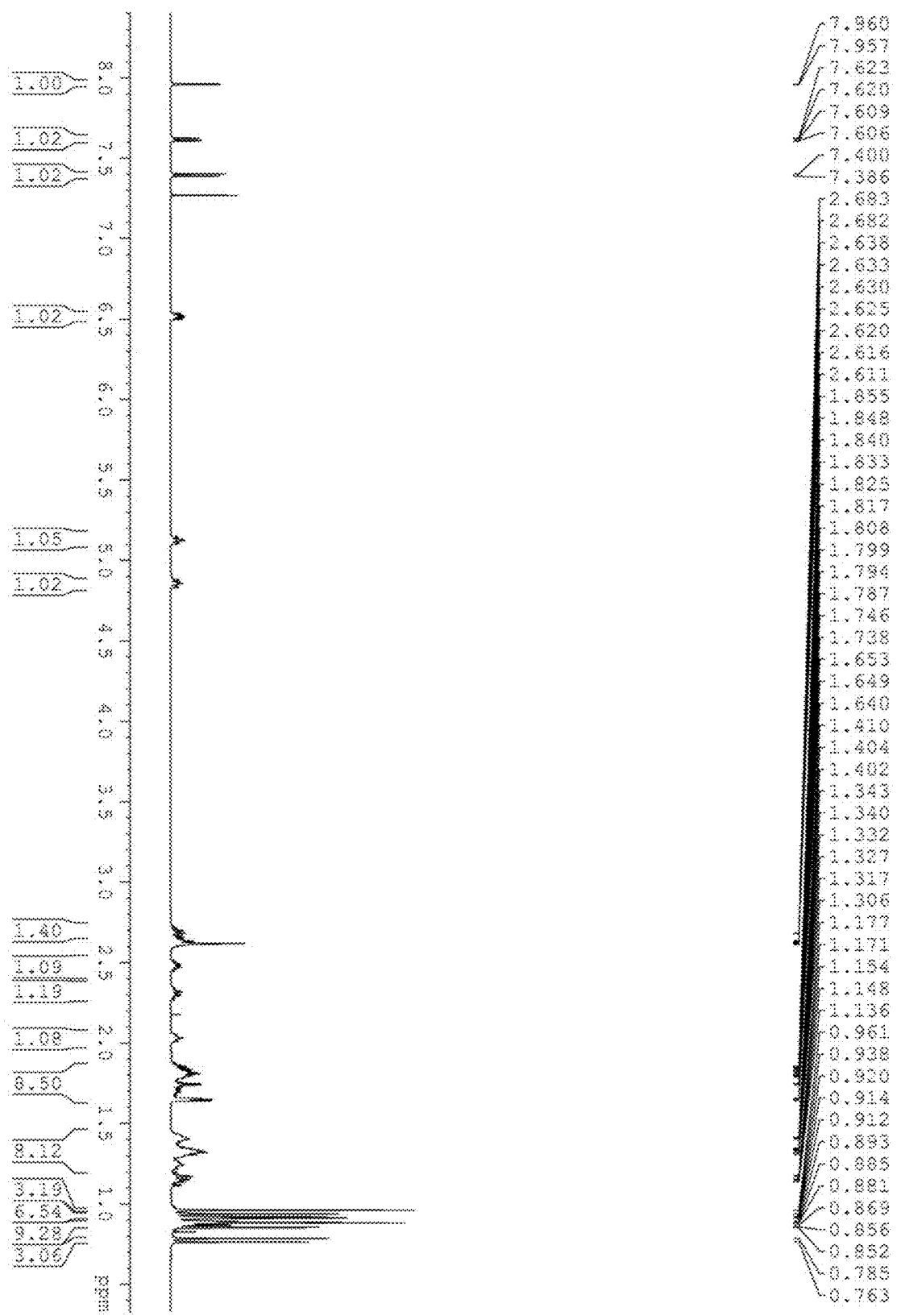
FIG. 21 is a $^1$H-NMR spectrum of compound 9 in Example 9.
Figure 22:
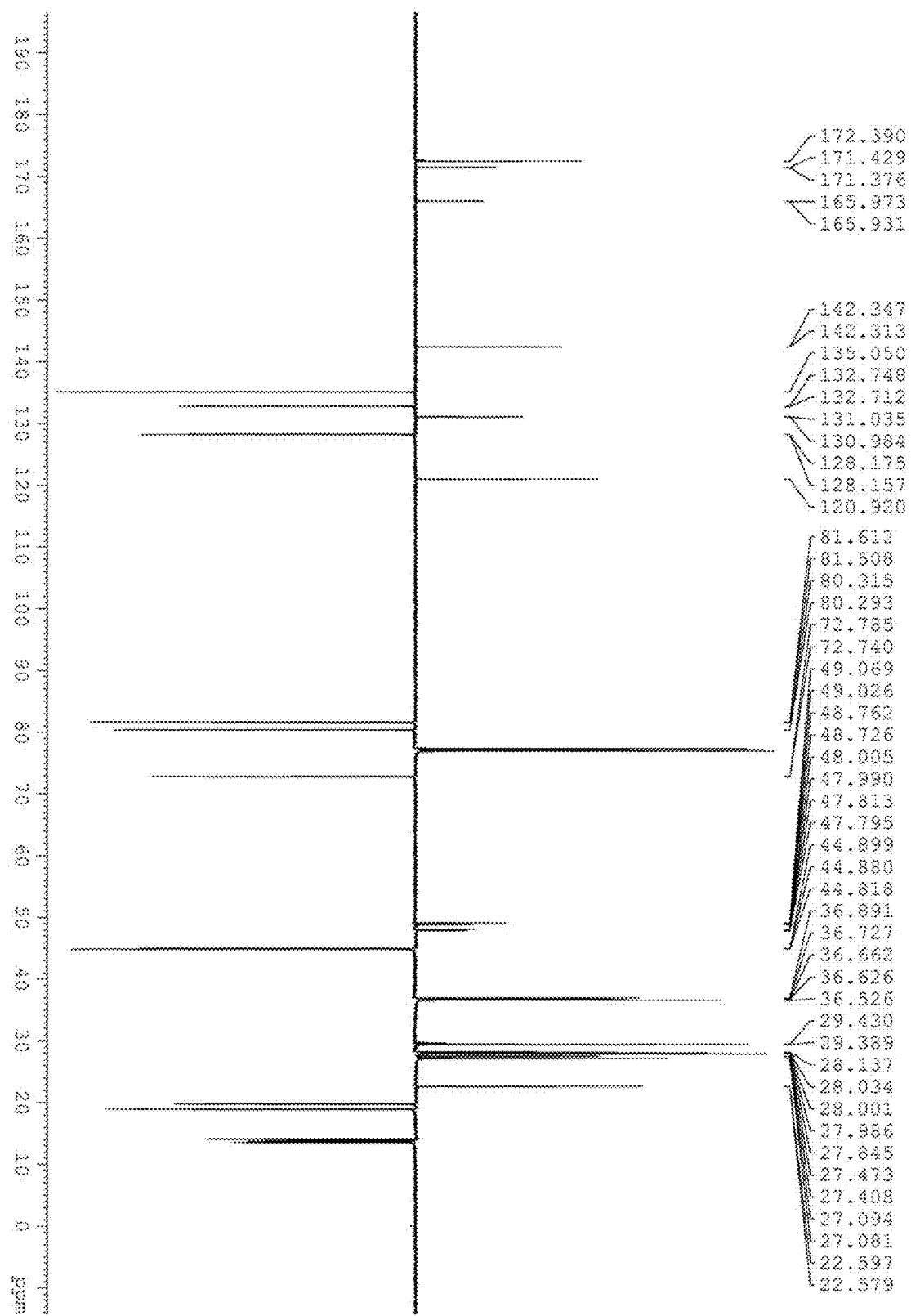
FIG. 22 is a $^{13}$C-APT spectrum of compound 9 in Example 9.
Figure 23:
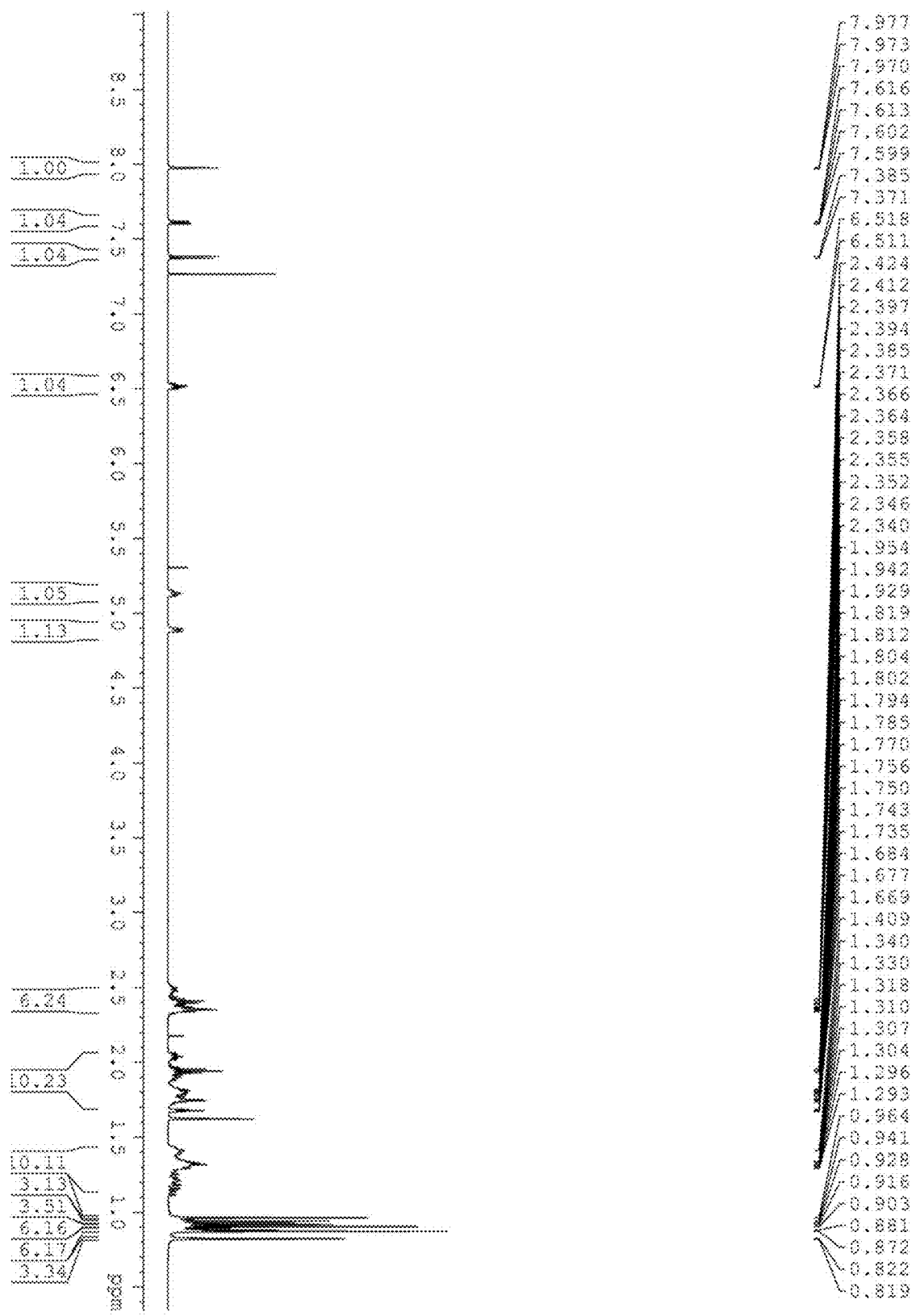
FIG. 23 is a $^1$H-NMR spectrum of compound 10 in Example 10.
Figure 24:
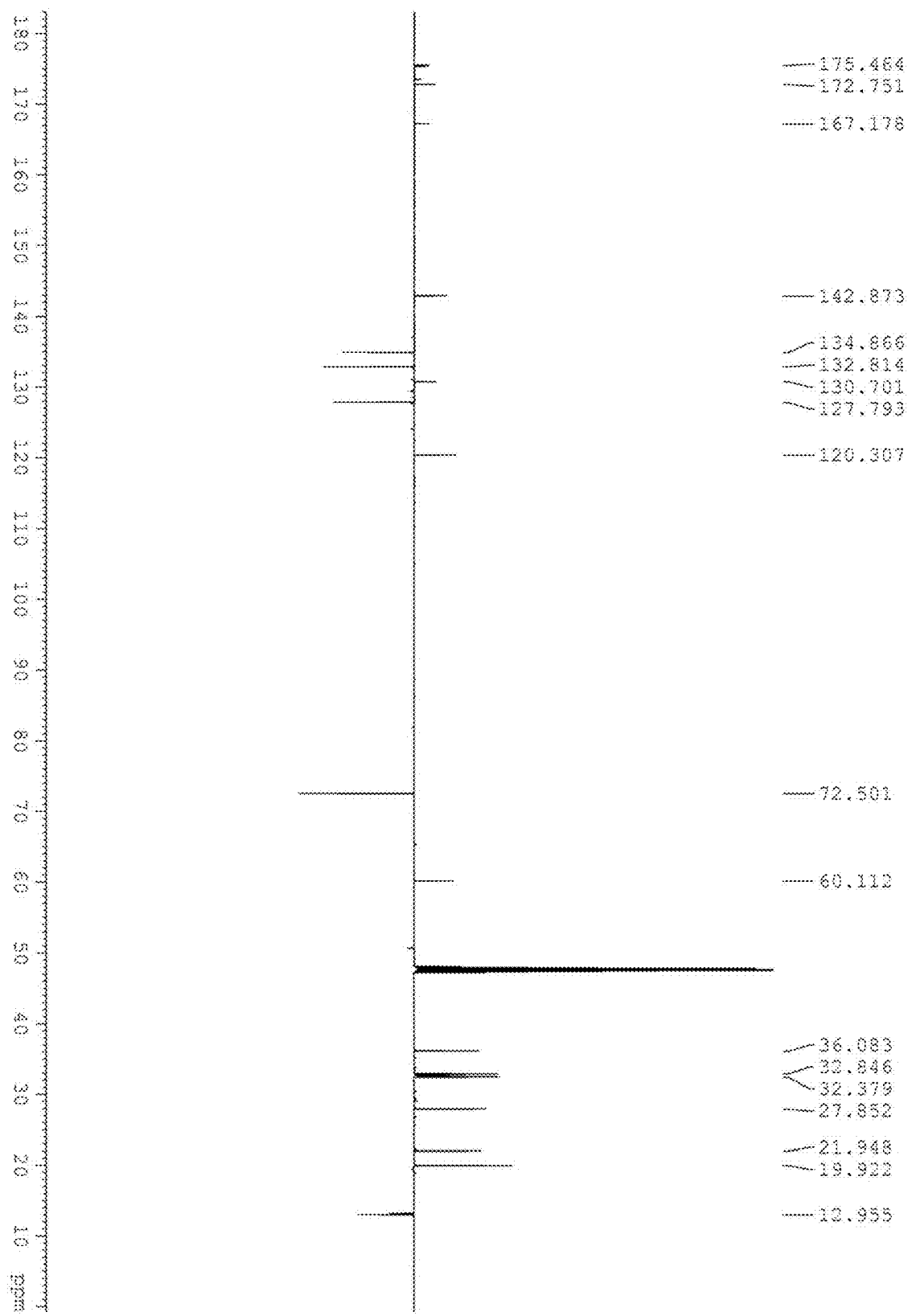
FIG. 24 is a $^{13}$C-APT spectrum of compound 10 in Example 10.
Figure 25:
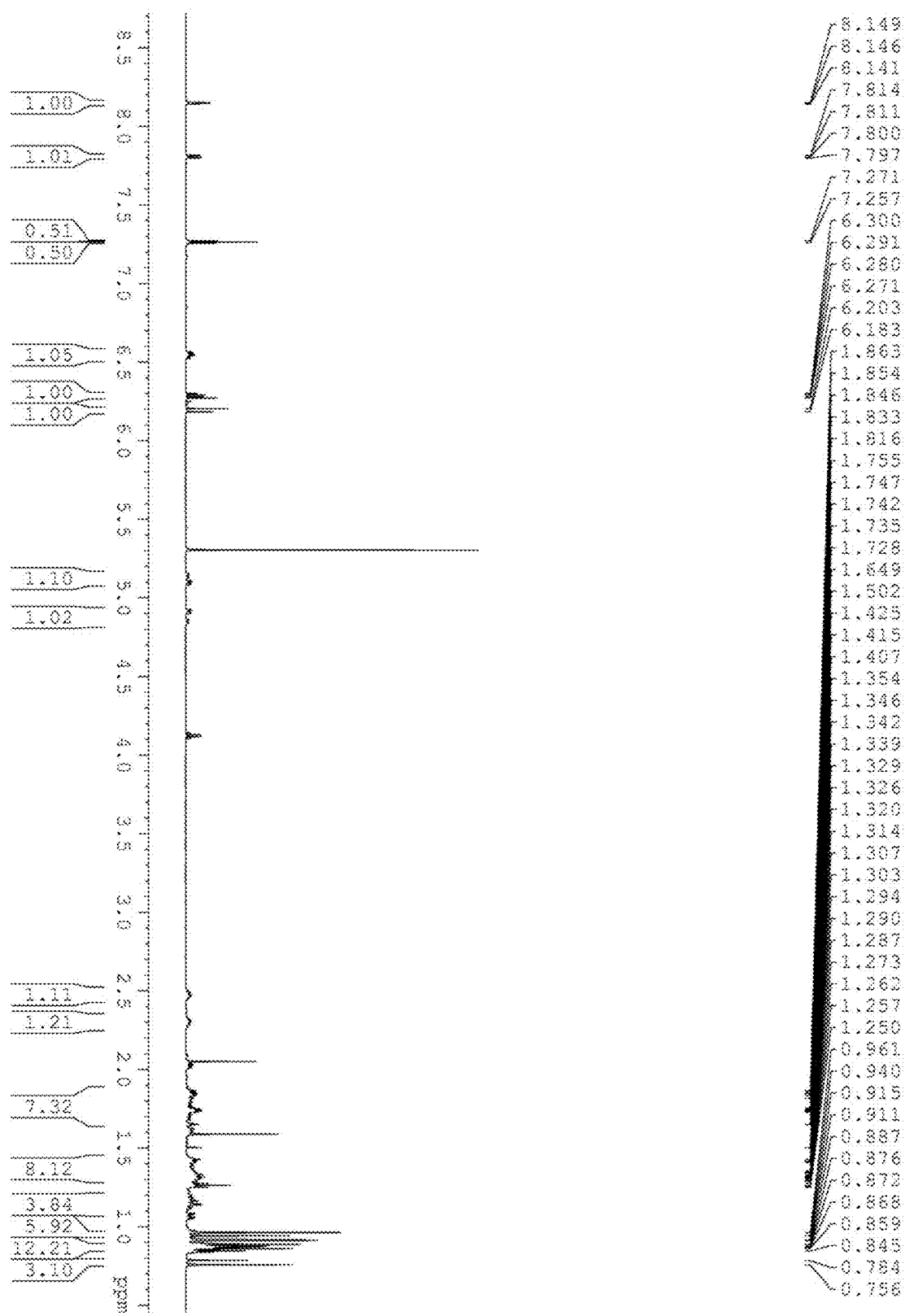
FIG. 25 is a $^1$H-NMR spectrum of compound 11 in Example 11.
Figure 26:
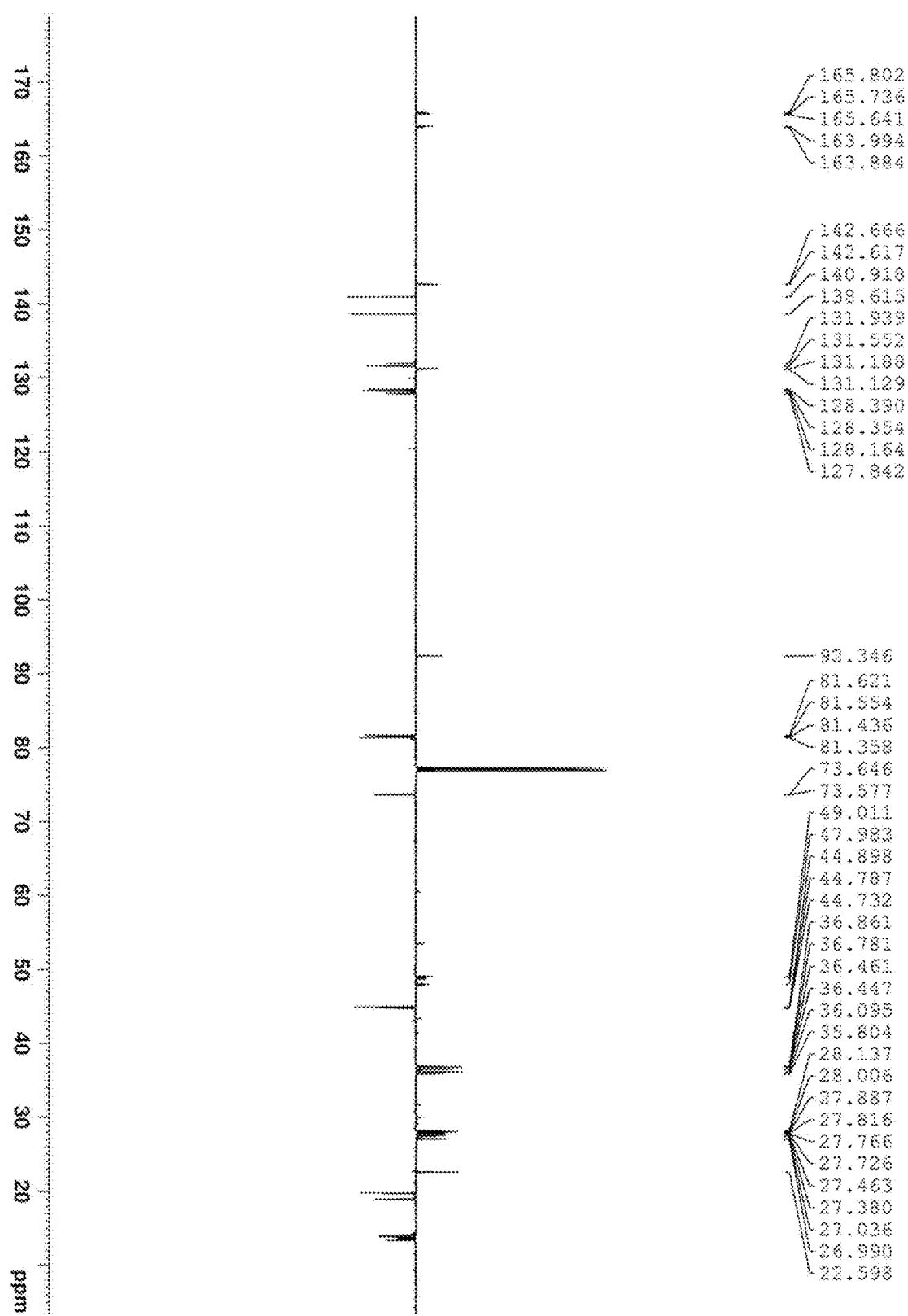
FIG. 26 is a $^{13}$C-APT spectrum of compound 11 in Example 11.
Figure 27:
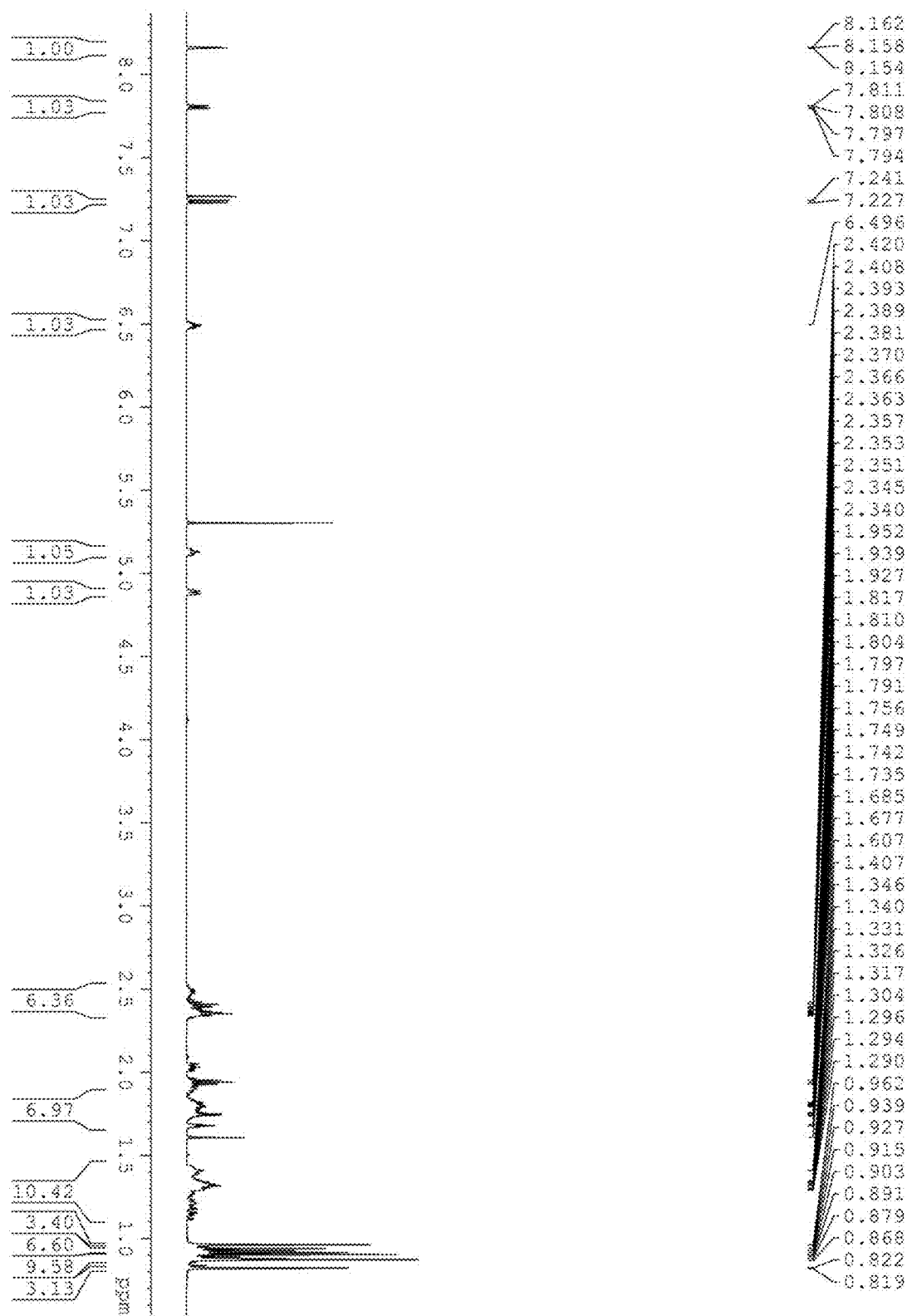
FIG. 27 is a $^1$H-NMR spectrum of compound 12 in Example 12.
Figure 28:
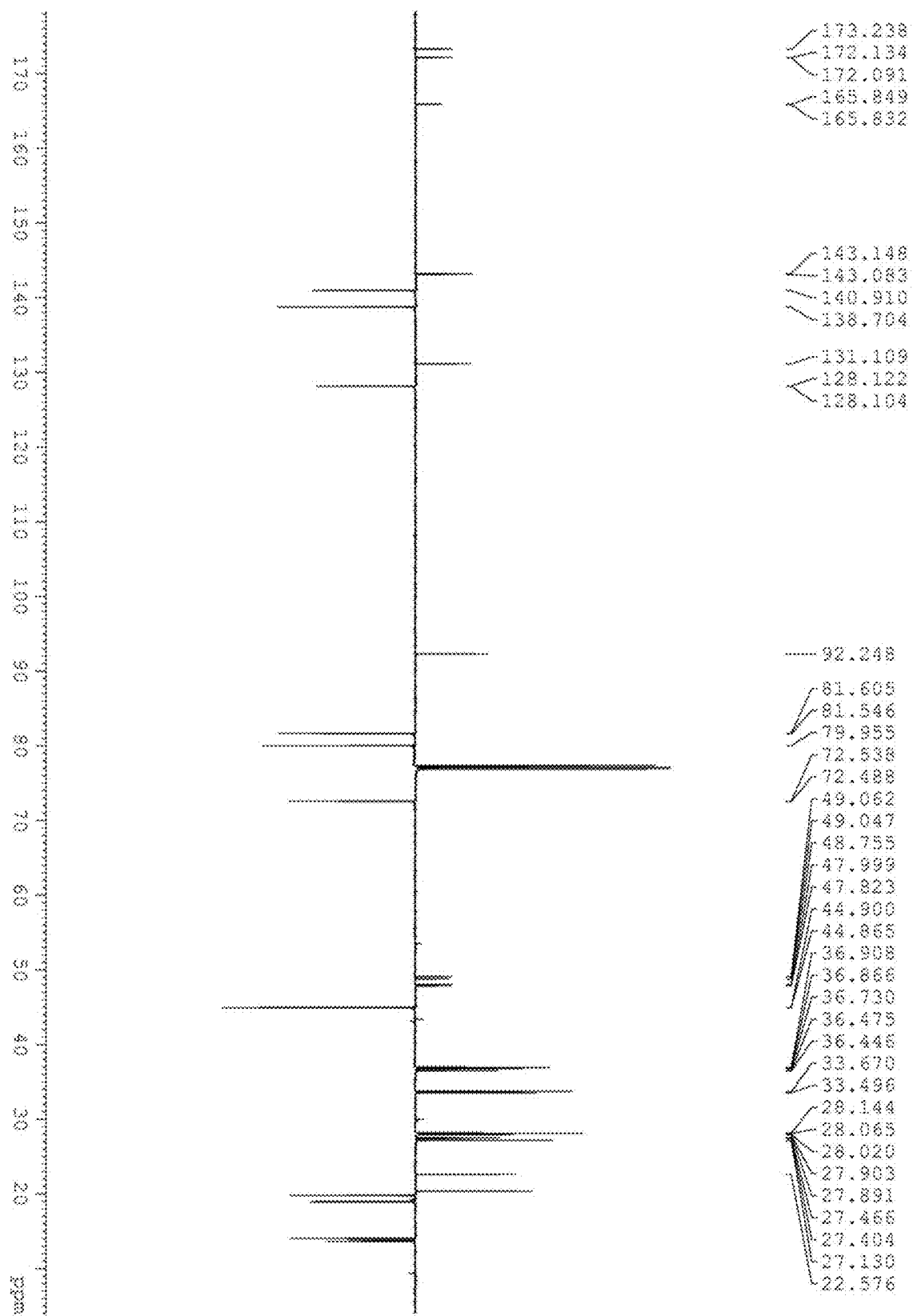
FIG. 28 is a $^{13}$C-APT spectrum of compound 12 in Example 12.

5.0 g of n-butylidenephthalide (26.6 mmol) was dissolved in 50 mL of anhydrous ethanol, 250 mg of 10% Pd/C was added, hydrogen gas was introduced under normal pressure, and the mixture reacted at room temperature for 2-3 hours. TLC was used to monitor the reaction, and the developer condition was petroleum ether: ethyl acetate (8:1). After the reaction was completed, the reacted mixture was filtered, the filtrate was collected, and the solvent was removed by rotary evaporation to obtain 5.0 g of yellow oily liquid R-2 in a yield of 98.9%. The $^1$H-NMR and $^{13}$C-NMR data of compound R-2 are shown below.

$^1$H-NMR (600 MHz, CDCl$_3$) δ: 7.88 (d, J=7.6 Hz, 1H, H-6), 7.55 (td, J=7.6, 7.2, 1.0 Hz, 1H, H-4), 7.51 (t, J=7.6, 7.2 Hz, 1H, H-5), 7.43 (dd, J=7.6, 0.6 Hz, 1H, H-3), 5.47 (m, 1H, —C(CH)O—), 2.06-2.01 (m, 1H, —CHCH$_2$—), 1.78-1.72 (m, 1H, —CHCH$_2$—), 1.49-1.33 (m, 4H, —CH$_2$CH$_2$CH$_3$), 0.90 (t, J=7.5 Hz, 3H, —CH$_3$); $^{13}$C-NMR (150 MHz, CDCl$_3$) δ: 170.8, 150.1, 134.0, 129.0, 126.1, 125.6, 121.8, 81.5, 34.4, 26.9, 22.4, 13.9.

Preparation of Intermediate R-3

Compound R-2 (5.0 g, 26.3 mmol) was added into 30 mL of ethanol-water mixed solution (volume ratio 2:1), potassium hydroxide (2.0 g, 35.6 mmol) was added therein, microwave reaction was conducted at 70° C. for 30 min (or heating reflux reaction was conducted for 2 h), the solvent was removed by rotary evaporation after the completion of the reaction, the concentrated solution was diluted with water, the pH was adjusted to 3-4 with dilute hydrochloric acid, white solid was separated out and extracted three times with ethyl acetate, the organic layers was combined and dried with anhydrous magnesium sulfate to obtain an ethyl acetate solution of compound R-3, which was used directly for the next reaction.

Preparation of Intermediate R-4

Succinic anhydride (3.4 g, 28.8 mmol) was added into the ethyl acetate solution of compound R-3, DMAP (240 mg, 2.0 mmol) was added, then triethylamine (4 mL, 28.8 mmol) was dropped therein, and the mixture was stirred for reaction. After the reaction was completed, water was added for extraction, the organic layer was collected and dried with anhydrous sodium sulfate, filtered, and the solvent was evaporated to dryness, which is directly used for the next step of the reaction. The $^1$H NMR and $^{13}$C NMR data of compound R-4 are shown below.

¹H-NMR (600 MHz, CDCl₃) δ: 8.10 (dd, J=8.2, 1.0 Hz, 1H, H-3), 7.55 (td, J=7.9, 6.9, 1.0 Hz, 1H, H-5), 7.52 (dd, J=7.8, 1.4 Hz, 1H, H-6), 7.34 (td, J=8.1, 6.6, 1.6 Hz, 1H, H-4), 6.62 (m, 1H, —C(CH)O—), 2.74-2.64 (m, 4H, —COCH₂CH₂COOH), 1.86-1.80 (m, 2H, —OCHCH₂—), 1.44-1.29 (m, 4H, —CH₂CH₂CH₃), 0.88 (t, J=7.5 Hz, 3H, —CH₃); ¹³C-NMR (150 MHz, CDCl₃) δ: 178.6, 172.4, 171.6, 144.3, 133.3, 131.3, 127.3, 127.0, 126.1, 73.6, 36.5, 29.7, 29.0, 27.9.

Example 1: Preparation of Compound 1 (i.e. R-5 in Synthesis Route 1)

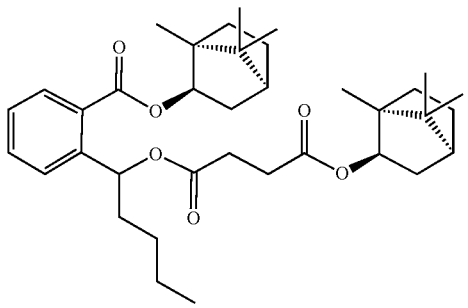 [SMILES: CCCCC(OC(=O)CCC(=O)O[C@@H]1C[C@@H]2CC[C@@]1(C)C2(C)C)c1ccccc1C(=O)O[C@@H]1C[C@@H]2CC[C@@]1(C)C2(C)C]

Compound R-4 (2.57 g, 8.3 mmol) was dissolved into 30 mL of dichloromethane at 0° C., DCC (4.3 g, 20.8 mmol) and DMAP (0.64 g, 5.2 mmol) were added therein, the mixture was stirred at 0° C. for 30 min, then dexborneol (3.2 g, 20.7 mmol) was added, and the resulting mixture was transferred to room temperature for reaction and stirred overnight. After the reaction was completed, the filtrate was collected and concentrated. The concentrated solution was left standing at 4° C. for 2 hours, filtered by suction, and the filtrate was subjected to column chromatography with petroleum ether: ethyl acetate (6:1) to obtain 3.59 g of light yellow viscous liquid, with a yield of 82.3%. The ¹H NMR and ¹³C NMR data of compound R-5 are shown below.

¹H-NMR (600 MHz, CDCl₃) δ: 7.89 (d, J=7.2 Hz, 1H, H-3), 7.52-7.49 (m, 2H, H-5, 6), 7.34 (m, 1H, H-4), 6.62 (m, 1H, C(CH)O), 5.12 (m, 1H, COOCH), 4.86 (m, 1H, COOCH), 2.75-2.60 (m, 4H, —COCH₂CH₂COOH), 0.97-0.85 (m, 21H, CH₃×7); ¹³C-NMR (150 MHz, CDCl₃) δ: 172.4, 171.43, 171.38, 167.24, 167.21, 143.40, 143.38, 132.1, 130.14, 130.12, 129.14, 129.10, 127.1, 126.2, 80.96, 80.88, 80.26, 80.25, 73.25, 73.20, 49.0, 48.76, 48.73, 47.95, 47.92, 47.91, 47.80, 44.95, 44.93, 44.8, 37.0, 36.8, 36.67, 36.62, 34.9, 29.50, 29.48, 28.1, 28.0, 27.6, 27.50, 27.48, 27.0, 25.5, 22.65, 22.63, 19.77, 19.71, 18.99, 18.95, 14.0, 13.8, 13.6, 13.50, 13.48.

Preparation of Intermediate L-1

Compound R-2 (32.8 g, 172.5 mmol) was dissolved in methanol, potassium hydroxide aqueous solution was added therein, and microwave reaction was conducted at 60° C. for 1 h. After the reaction was completed, the methanol was evaporated, the concentrated solution was diluted, and the pH was adjusted to 3-4 with dilute hydrochloric acid at −10° C. After extraction with ethyl acetate, (-)-α-phenethylamine (20.7 g, 171.2 mmol) was added into the organic layer, and allowed to stand at −10° C. for 5 to 10 min, and then continued to stand at room temperature for 5 to 10 h, and white optically active amine salt crystals were collected. The white crystals were recrystallized with methanol/ethyl acetate mixed solvent for 2-3 times, the obtained needle shaped crystals were dissolved in water, 2N potassium hydroxide was added for dissociation, the water layer was collected after ethyl acetate extraction, the pH was adjusted to 1-2 with dilute hydrochloric acid, extracted with ethyl acetate, the organic phase was dried and filtered, and concentrated to obtain 12.2 g of compound L-1, with a yield of 37.2%.

Example 2: Preparation of Compound 2 (i.e. L-4 in Synthesis Route 2)

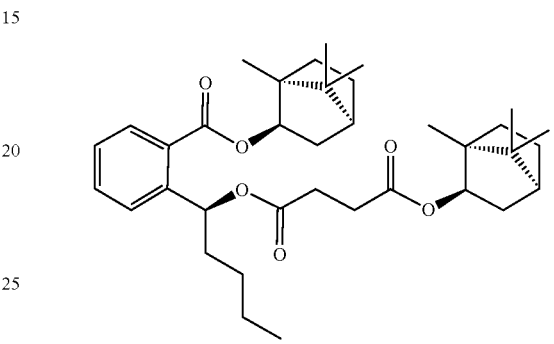

The synthesis of compounds L-2, L-3, and L-4 (Example 2) refers to the synthesis of R-3, R-4, and R-5 in Example 1. The product L-4 in this example was a light yellow oily liquid, and the ¹H NMR and ¹³C NMR data are shown below.

¹H-NMR (600 MHz, CDCl₃) δ: 7.89 (d, J=7.2 Hz, 1H, H-3), 7.53-7.48 (m, 2H, H-5, 6), 7.32 (m, 1H, H-4), 6.63 (m, 1H, C(CH)O), 5.13 (m, 1H, COOCH), 4.85 (m, 1H, COOCH), 2.74-2.61 (m, 4H, —COCH₂CH₂COOH), 0.96-0.85 (m, 21H, CH₃×7); ¹³C-NMR (150 MHz, CDCl₃) δ: 172.5, 171.4, 167.2, 143.3, 132.1, 129.1, 127.1, 126.2, 80.9, 80.3, 73.2, 49.0, 48.7, 47.9, 47.8, 44.9, 44.8, 37.0, 36.8, 36.7, 29.5, 29.4, 28.1, 28.0, 27.9, 27.4, 27.1, 22.6, 19.8, 19.7, 18.9, 18.8, 14.0, 13.6, 13.5.

Example 3: Preparation of Compound 3

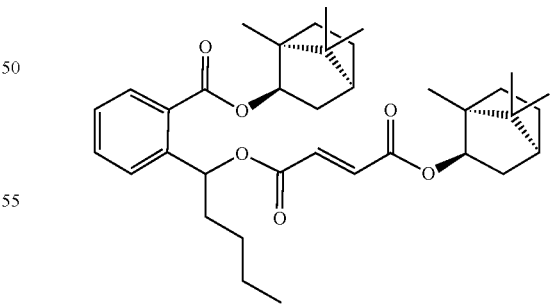

Referring to Example 1, only the succinic anhydride in the synthesis of compound R-4 was replaced with maleic anhydride, and the product was a light yellow oily liquid with a yield of 80.3%. The ¹H NMR and ¹³C NMR data of the product are shown below.

¹H-NMR (600 MHz, CDCl₃) δ: 7.92 (m, 1H, H-3), 7.54-7.50 (m, 2H, H-5, 6), 7.34 (m, 1H, H-4), 6.89 (m, 2H,

CH=CH), 6.74 (m, 1H, C(CH)O), 5.52-5.13, 5.01-4.99 (m, 2H, COOCH×2), 0.98-0.85 (m, 21H, CH$_3$×7); $^{13}$C-NMR (150 MHz, CDCl$_3$) δ: 166.13, 166.11, 164.3, 163.31, 163.28, 141.78, 141.73, 133.1, 132.4, 131.1, 129.17, 129.15, 128.15, 128.12, 126.3, 125.11, 125.10, 80.1, 79.98, 79.92, 72.98, 72.95, 48.00, 47.92, 46.90, 46.88, 43.90, 43.87, 43.8, 35.9, 35.8, 35.7, 35.67, 35.60, 33.9, 27.1, 26.98, 26.96, 26.9, 26.44, 26.38, 26.1, 24.4, 21.56, 21.53, 18.72, 18.65, 17.89, 17.80, 13.0, 12.7, 12.6, 12.49, 12.48.

Example 4: Preparation of Compound 4

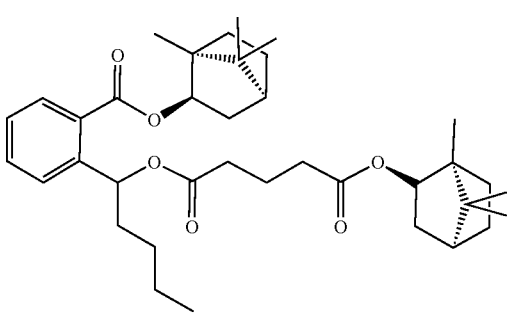

Referring to Example 1, only the succinic anhydride in the synthesis of compound R-4 was replaced with glutaric anhydride, and the product was a light yellow oily liquid with a yield of 69.5%. The $^1$H NMR and $^{13}$C NMR data of the product are shown below.

$^1$H-NMR (600 MHz, CDCl$_3$) δ: 7.90 (m, 1H, H-3), 7.51-7.50 (m, 2H, H-5, 6), 7.32 (m, 1H, H-4), 6.60 (m, 1H, C(CH)O), 5.13, 4.89 (m, 2H, COOCH×2), 0.98-0.82 (m, 21H, CH$_3$×7); $^{13}$C-NMR (150 MHz, CDCl$_3$) δ: 173.3, 172.18, 172.13, 167.2, 143.64, 143.54, 132.0, 130.2, 131.1, 129.1, 127.1, 126.1, 80.94, 80.90, 79.9, 72.94, 72.87, 49.0, 48.7, 47.9, 47.8, 44.9 (d, J=4.4 Hz), 44.8, 37.0, 36.9, 36.8, 36.85, 36.80, 33.8, 33.6, 28.05, 28.02, 27.1, 22.63, 22.60, 20.4, 20.3, 19.8, 18.95, 18.86, 14.0, 13.8, 13.6, 13.5.

Example 5: Preparation of Compound 5

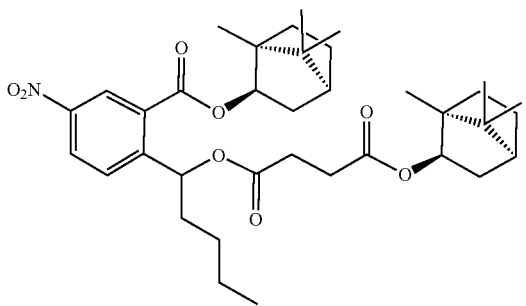 [SMILES: CCCCC(OC(=O)CCC(=O)O[C@@H]1C[C@@H]2CC[C@@]1(C)C2(C)C)c1ccc([N+](=O)[O-])cc1C(=O)O[C@@H]1C[C@@H]2CC[C@@]1(C)C2(C)C]

Referring to Example 1, only butylphthalide was replaced with 3-nitro butylphthalide, and the product was a light yellow oily liquid with a yield of 74.5%. The $^1$H NMR and $^{13}$C NMR data of the product are shown below.

$^1$H-NMR (600 MHz, CDCl$_3$) δ: 8.71 (d, J=2.4 Hz, 1H, H-6), 8.33 (dd, J=8.7, 2.4 Hz, 1H, H-5), 7.72 (d, J=8.6 Hz, 1H, H-3), 6.59 (m, 1H, C(CH)O), 5.17, 4.86 (m, 2H, COOCH×2), 0.96-0.80 (m, 21H, CH$_3$×7); $^{13}$C-NMR (150 MHz, CDCl$_3$) δ: 172.3, 171.56, 171.50, 165.25, 165.21, 150.51, 150.49, 146.6, 130.30, 130.28, 127.7, 126.5, 125.32, 125.31, 82.2, 82.1, 80.4, 72.83, 72.79, 48.76, 48.74, 48.06, 48.04, 47.8, 44.89, 44.87, 44.8, 36.9, 36.7, 36.67, 36.63, 36.40, 36.38, 33.9, 29.30, 29.27, 28.1, 28.00, 27.9, 27.47, 27.41, 27.1, 22.52, 22.50, 19.76, 19.69, 18.92, 18.83, 14.0, 13.8, 13.6, 13.51, 13.46.

Example 6: Preparation of Compound 6

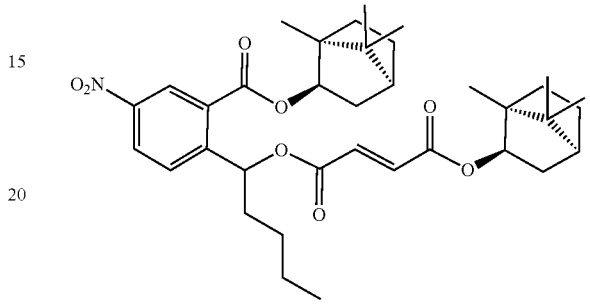

Referring to Example 1, only butylphthalide was replaced with 3-nitro-butylphthalide, and succinic anhydride in the synthesis of compound R-4 was replaced with maleic anhydride, and the product was a light yellow oily liquid with a yield of 80.2%. The $^1$H NMR and $^{13}$C NMR data of the product are shown below.

$^1$H-NMR (600 MHz, CDCl$_3$) δ: 8.71 (m, 1H, H-6), 8.33 (dd, J=2.40, 8.62 Hz, 1H, H-5), 7.74 (m, 1H, H-3), 6.89 (m, 2H, CH=CH), 6.65 (m, 1H, C(CH)O), 6.32, 6.23 (m, 2H, CH=CH), 5.17, 4.89 (m, 2H, COOCH×2), 0.98-0.74 (m, 21H, CH$_3$×7); $^{13}$C-NMR (150 MHz, CDCl$_3$) δ: 172.3, 173.06, 172.88, 153.4, 136.9, 133.2, 130.9, 128.86, 128.72, 127.6, 121.3, 80.14, 80.12, 79.9, 65.6, 60.4, 50.0, 48.7, 47.8, 44.86, 44.84, 36.90, 36.85, 36.4, 33.77, 33.71, 33.62, 33.53, 33.4, 32.4, 30.6, 29.27, 28.10, 28.09, 28.04, 27.1, 26.07, 25.98, 25.42, 25.38, 25.0, 24.8, 22.5, 20.34, 20.30, 19.7, 18.8, 14.2, 14.0, 13.57, 13.54.

Example 7: Preparation of Compound 7

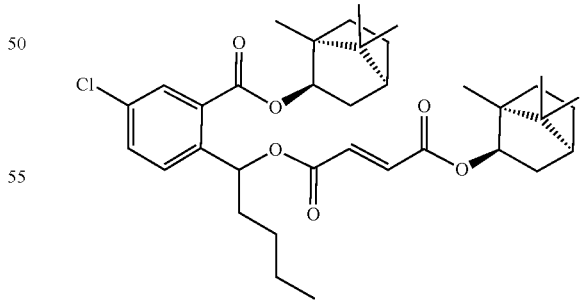

Referring to Example 1, only butylphthalide was replaced with 3-chloro-butylphthalide, and succinic anhydride in the synthesis of compound R-4 was replaced with maleic anhydride, and the product was a light yellow oily liquid with a yield of 72.1%. The $^1$H NMR and $^{13}$C NMR data of the product are shown below.

¹H-NMR (600 MHz, CDCl₃) δ: 7.85 (m, 1H, H-6), 7.47 (m, 2H, H-3, 5), 6.87 (m, 2H, C$\underline{H}$=C$\underline{H}$), 6.67 (m, 1H, C(CH)O), 5.15, 4.99 (m, 2H, COOC$\underline{H}$×2), 0.94-0.85 (m, 21H, CH₃×7); ¹³C-NMR (150 MHz, CDCl₃) δ: 166.0, 165.0, 165.3, 164.30, 164.29, 141.31, 141.28, 134.4, 133.7, 133.2, 133.1, 132.23, 132.14, 130.82, 130.80, 129.9, 127.83, 137.82, 81.6, 81.5, 81.26, 81.17, 73.8, 73.4, 49.06, 48.99, 48.01, 47.95, 44.90, 44.89, 36.9, 36.7, 36.7, 36.4, 28.1, 28.0, 28.0, 27.2, 27.49, 27.43, 27.15, 27.14, 22.57, 22.54, 19.77, 19.71, 18.9, 18.8, 14.0, 13.8, 13.6, 13.5.

Example 8: Preparation of Compound 8

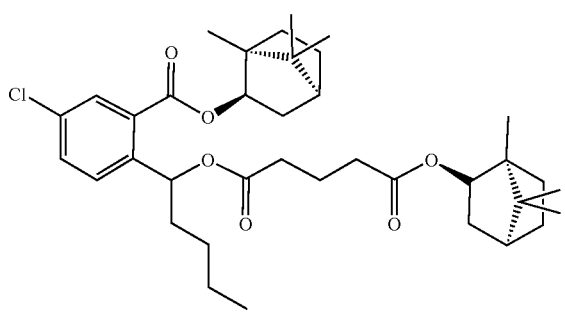

Referring to Example 1, only butylphthalide was replaced with 3-chloro-butylphthalide, and succinic anhydride in the synthesis of compound R-4 was replaced with glutaric anhydride, and the product was a light yellow oily liquid with a yield of 55.4%. The ¹H NMR and ¹³C NMR data of the product are shown below.

¹H-NMR (600 MHz, CDCl₃) δ: 7.83 (m, 1H, H-6), 7.45 (m, 2H, H-3, 5), 6.53 (m, 1H, C(CH)O), 5.15, 4.88 (m, 2H, COOC$\underline{H}$×2), 0.96-0.82 (m, 21H, CH₃×7); ¹³C-NMR (150 MHz, CDCl₃) δ: 173.3, 172.14, 172.10, 166.03 166.01, 142.12, 142.05, 135.0, 133.0, 132.1, 130.7, 129.9, 127.78, 127.77, 81.57, 51.49, 80.0, 72.42, 72.27, 49.1, 48.6, 48.0, 47.8, 44.91, 44.89, 44.8, 36.9, 36.8, 36.7, 36.56, 36.54, 33.7, 33.5, 28.1, 28.15, 28.06, 27.9, 27.48, 27.42, 22.57, 22.55, 20.3, 19.76, 19.73, 18.93, 19.86, 14.0, 13.8, 13.6, 13.5.

Example 9: Preparation of Compound 9

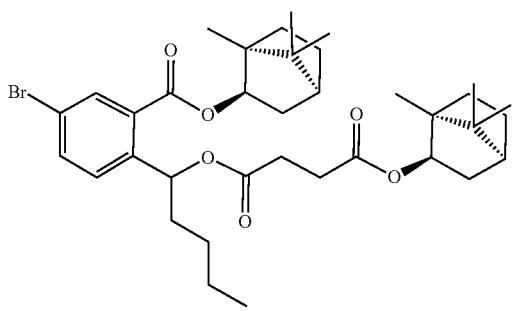 [SMILES: CCCCC(OC(=O)/C=C/C(=O)O[C@@H]1C[C@@H]2CC[C@@]1(C)C2(C)C)c1ccc(Cl)cc1C(=O)O[C@@H]1C[C@@H]2CC[C@@]1(C)C2(C)C]

Referring to Example 1, only butylphthalide was replaced with 3-bromobutylphthalide, and the product was a light yellow oily liquid with a yield of 86.2%. The ¹H NMR and ¹³C NMR data of the product are shown below.

¹H-NMR (600 MHz, CDCl₃) δ: 7.96 (d, J=2.0 Hz, 1H, H-6), 7.61 (dd, J=8.3, 2.0 Hz, 1H, H-5), 7.39 (d, J=8.4 Hz, 1H, H-3), 6.51 (m, 1H, C(CH)O), 5.12, 4.86 (m, 2H, COOC$\underline{H}$×2), 0.96-0.76 (m, 21H, CH₃×7); ¹³C-NMR (150 MHz, CDCl₃) δ: 172.4, 171.43, 171.38, 165.97, 165.93, 142.35, 142.31, 135.0, 132.75, 132.71, 131.03, 130.98, 128.17, 128.16, 120.9, 81.6, 81.5, 80.32, 80.29, 72.78, 72.74, 49.07, 49.23, 48.76, 48.73, 48.00, 47.99, 47.81, 47.80, 44.90, 44.81, 44.8, 36.9, 36.7, 36.66, 36.63, 36.5, 29.43, 29.39, 28.1, 28.03, 28.00, 27.9, 27.8, 27.5, 27.4, 27.09, 27.08, 22.59, 22.58, 19.76, 19.70, 18.93, 18.84, 14.0, 13.8, 13.6, 13.49, 13.47.

Example 10: Preparation of Compound 10

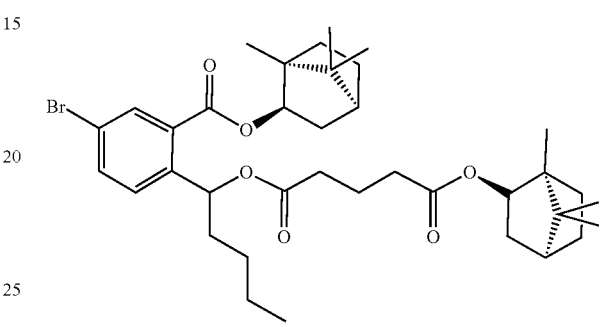

Referring to Example 1, only the butylphthalide was replaced with 3-bromo-butylphthalide, and the succinic anhydride in the synthesis of compound R-4 was replaced with glutaric anhydride, and the product was a light yellow oily liquid with a yield of 50.1%. The ¹H NMR and ¹³C NMR data of the product are shown below.

¹H-NMR (600 MHz, CDCl₃): 7.97 (m, 1H, H-6), 7.61 (dd, J=8.7, 2.4 Hz, 1H, H-5), 7.34 (d, J=8.4 Hz, 1H, H-3), 6.51 (m, 1H, C(CH)O), 5.13, 4.89 (m, 2H, COOC$\underline{H}$×2), 0.96-0.82 (m, 21H, CH₃×7); ¹³C-NMR (150 MHz, CDCl₃) δ: 173.2, 172.14, 172.10, 165.94, 165.93, 142.58, 142.51, 135.0, 132.8, 130.9, 128.03, 128.02, 120.9, 81.6, 81.5, 79.9, 72.46, 72.41, 49.06, 49.05, 48.8, 48.0, 47.8, 44.90, 44.84, 36.92, 32.86, 36.7, 36.51, 36.48, 33.7, 33.5, 28.1, 28.06, 28.02, 27.9, 27.5, 27.48, 27.42, 27.1, 22.57, 22.55, 20.3, 19.77, 19.73, 18.93, 18.86, 14.0, 13.8, 13.6, 13.5.

Example 11: Preparation of Compound 11

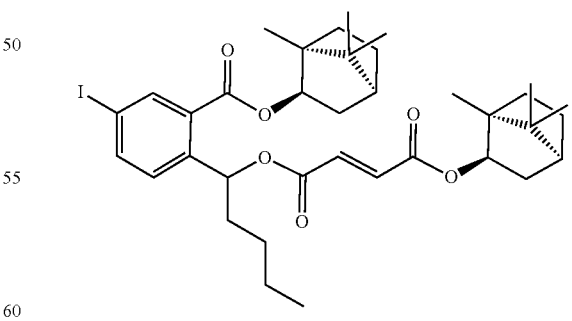

Referring to Example 1, only the butylphthalide was replaced with 3-iodo-butylphthalide, and the succinic anhydride in the synthesis of compound R-4 was replaced with maleic anhydride, and the product was a light yellow oily liquid with a yield of 61.3%. The ¹H NMR and ¹³C NMR data of the product are shown below.

¹H-NMR (600 MHz, CDCl₃) δ: 8.45 (m, 1H, H-6), 7.81 (dd, J=8.4, 1.8 Hz, 1H, H-5), 7.26 (d, J=8.3 Hz, 1H, H-3), 6.54 (m, 1H, C(CH)O), 6.28, 6.19 (m, 2H, C$\underline{H}$=C$\underline{H}$), 5.12, 4.96 (m, 2H, COOC$\underline{H}$×2), 0.96-0.84 (m, 21H, CH₃×7); ¹³C-NMR (150 MHz, CDCl₃) δ: 165.81, 165.75, 165.6, 164.0, 142.66, 142.62, 140.9, 138.6, 131.9, 131.6, 131.19, 131.13, 128.39, 128.35, 128.2, 127.8, 92.4, 81.6, 81.5, 81.4, 81.3, 73.65, 73.58, 49.1, 48.8, 48.0, 47.8, 44.90, 44.78, 36.86, 36.78, 36.5, 36.1, 35.8, 33.7, 33.5, 28.1, 28.0, 27.9, 27.5, 27.46, 27.38, 27.0, 22.59, 22.58, 19.78, 19.69, 18.93, 18.85, 14.0, 13.8, 13.6, 13.4.

Example 12: Preparation of Compound 12

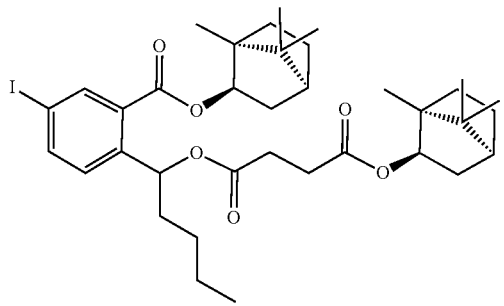 [SMILES: CCCCC(OC(=O)CCC(=O)O[C@@H]1C[C@@H]2CC[C@@]1(C)C2(C)C)c1ccc(I)cc1C(=O)O[C@@H]1C[C@@H]2CC[C@@]1(C)C2(C)C]

Referring to Example 1, only the butylphthalide was replaced with 3-iodo-butylphthalide, and the succinic anhydride in the synthesis of compound R-4 was replaced with glutaric anhydride. The product was a light yellow oily liquid with a yield of 51.1%. The ¹H NMR and ¹³C NMR data of the product are shown below.

¹H-NMR (600 MHz, CDCl₃) δ: 8.16 (m, 1H, H-6), 7.80 (dd, J=8.2, 1.8 Hz, 1H, H-5), 7.23 (d, J=8.2 Hz, 1H, H-3), 6.49 (m, 1H, C(CH)O), 5.13, 4.89 (m, 2H, COOCH×2), 0.96-0.82 (m, 21H, CH₃×7); ¹³C-NMR (150 MHz, CDCl₃) δ: 173.2, 172.13, 172.09, 165.85, 165.83, 143.15, 148.08, 140.9, 138.7, 131.1, 130.9, 128.12, 128.10, 92.4, 81.6, 81.5, 79.9, 72.54, 72.49, 49.06, 49.05, 48.8, 48.0, 47.8, 44.90, 44.86, 36.91, 36.86, 36.7, 36.48, 36.45, 33.7, 33.5, 28.1, 28.06, 28.02, 27.90, 27.89, 27.5, 27.47, 27.40, 27.1, 22.58, 22.56, 20.3, 19.77, 19.73, 18.93, 18.86, 14.0, 13.8, 13.6, 13.5.

Pharmacodynamic Experiment: Study on the Preventive and Therapeutic Effects of NBP Derivatives (Compound 1 of Example 1 and Compound 2 of Example 2) on Cerebral Ischemia-reperfusion Injury I. Experimental method 1. Experimental grouping SHAM group: sham surgery group
Middle cerebral artery occlusion (MCAO) model group
Butylphthalide (NBP): 5 mg/kg
Levobutylphthalide (L-NBP): 2.5 mg/kg
NRB (Compound 1): 15 mg/kg (equivalent to a dose of 4.9 mg/kg of NBP through conversion)
Low dose of L-NRB (compound 2): 7.5 mg/kg (equivalent to a dose of 2.45 mg/kg of L-NBP through conversion)
High dose of L-NRB (compound 2): 15 mg/kg (equivalent to a dose of 4.9 mg/kg of L-NBP through conversion)
Aspirin group (ASP): 10 mg/kg 2. Administration Method The rats in the sham surgery group and the MCAO model group were administered the same amount of normal saline by intraperitoneal administration for 5 consecutive days before modeling, and then the MCAO operation was performed.

3. Modeling of Middle Cerebral Artery Occlusion (MCAO):

The middle cerebral artery occlusion (MCAO) model was made by thread-occlusion method. The operation process was strictly conducted in aseptic mode. The main operation process was as follows: the rat was anesthetized by intraperitoneal injection of chloral hydrate, the common carotid artery (CCA), external carotid artery (ECA) and internal carotid artery (ICA) were separated, the common carotid artery was clamped with a microarterial clamp, and the branches of the external carotid artery were electrocoagulated with a bipolar electrocoagulation pen. The main trunk of the external carotid artery was separated and ligated at a distance of 3-4 mm from the bifurcation of the common carotid artery. The internal carotid artery was temporarily clamped with a micro artery clamp. A small incision into the external carotid artery was cut with an ophthalmic scissors, and a 4-0 monofilament nylon thread coated with methylpolysiloxane was inserted. A loose knot was made at the incision of the external carotid artery to block the blood reflux of the internal carotid artery. The micro artery clamp of the internal carotid artery was removed, and the nylon thread is gently pushed into the internal carotid artery to reach the anterior cerebral artery in the skull, to block the opening of the middle cerebral artery (MCA), and the insert depth is approximately 18-22 mm. The microarterial clamp of the common carotid artery was removed, the subcutaneous tissue and skin were sutured layer by layer after disinfection, and the nylon thread was slowly draw out at 2 hours after operation, and the reperfusion was conducted. In the sham surgery group, all operations were the same except that nylon thread was not inserted. The rectal temperature of all rats was maintained at 37° C. throughout the entire experimental process.

II. Detection Indicators

1. Neurological Function Evaluation

After 24 hours of reperfusion, all rats were evaluated for neurobehavioral scores using the Longa 5-level scoring method. Longa scoring standard: 0, normal, without neurological impairment; 1, left forelimb extension disorder, weakened function; 2, circling to the left, paralysis of the left forelimb and severe impairment of function, and the rat keeps twisting towards the damaged area after lifting the rat's tail; 3, when walking, tilt to the left; 4, limb paralysis, unconscious consciousness.

2. Measurement of Cerebral Infarction Area:

After 24 hours of reperfusion, the cerebral infarction area was measured using tetrazolium red (TTC) staining. The rats were killed by cutting the neck, and the whole brain was quickly taken out. After being placed in the refrigerator at −20° C. for a short time and placed on the ice plate, and the olfactory bulb was removed. The forebrain was cut into six slices with a thickness of 2 mm along the coronal plane. The brain slices were placed in 1.5 mL of 2% TTC solution and incubated in dark for 30 minutes. Then the brain slices were fixed in 10% paraformaldehyde overnight, and then photographed for analysis. Use Image-J software to measure and calculate the volume of cerebral infarction.

III. Experimental Results

1. Neurological Function Score

Figure 29:
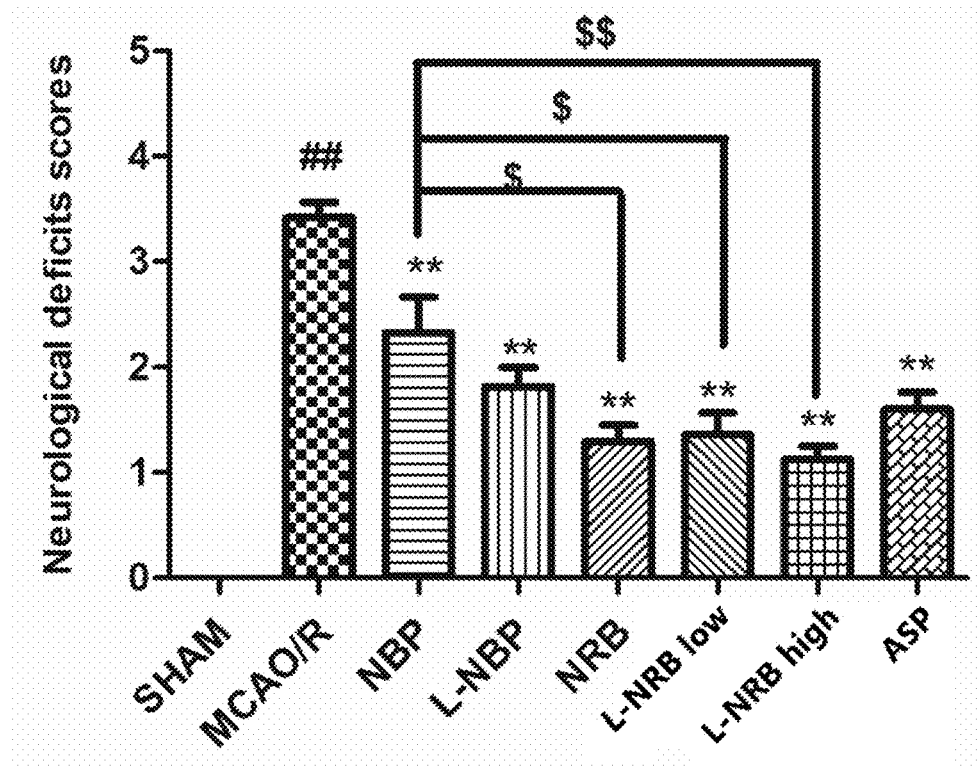
FIG. 29 demonstrates the effect of NBP derivatives on neural function scores in rats. (# #, p<0.01 vs sham group; **, p<0.01 vs MCAO/R group; $, p<0.05 vs NBP group; $$, p<0.01 vs NBP group).

The neurological function score of the model group was significantly higher than that of the sham surgery group. The neurological function scores of various administration group were significantly lower than those of the model group ($p<0.05$). Compared with the NBP group, the neurological function scores of NRB group ($p<0.05$), L-NRB low-dose group ($p<0.05$), and L-NRB high-dose group ($p<0.01$) showed significant reductions (FIG. 29, Table 1).

TABLE 1

Effects of NBP derivatives on neurological function scores in MCAO/R model rats

| group | dose (mg/kg) | neurological function scores | inhibition rate (vs model group) | efficiency (vs NBP group) | efficiency (vs L-NBP group) | efficiency (vs ASP group) |
|---|---|---|---|---|---|---|
| sham surgery group | — | 0.0 ± 0.0 | — | — | — | — |
| MCAO/R model group | — | 3.4 ± 0.5## | — | — | — | — |
| NBP group | 5 | 2.3 ± 1.0** | 32.4% | — | — | — |
| L-NBP group | 2.5 | 1.8 ± 0.6** | 47.1% | 21.7% | — | — |
| NRB group | 15 | 1.3 ± 0.5**$ | 61.8% | 43.5% | — | — |
| L-NRB low-dose group | 7.5 | 1.4 ± 0.7**$ | 58.8% | 39.1% | 22.2% | — |
| L-NRB high-dose group | 15 | 1.1 ± 0.4**$$& | 67.6% | 52.2% | 38.9% | 31.3% |
| ASP group | 10 | 1.6 ± 0.5** | 52.9% | — | — | — |

$P < 0.01$ vs sham surgery group;
**$P < 0.01$ vs MCAO/R model group;
$$P < 0.05$ vs NBP group;
$$$P < 0.01$ vs NBP group;
&$P < 0.01$ vs L-NBP group

2. Cerebral Infarction Area

Figure 30:
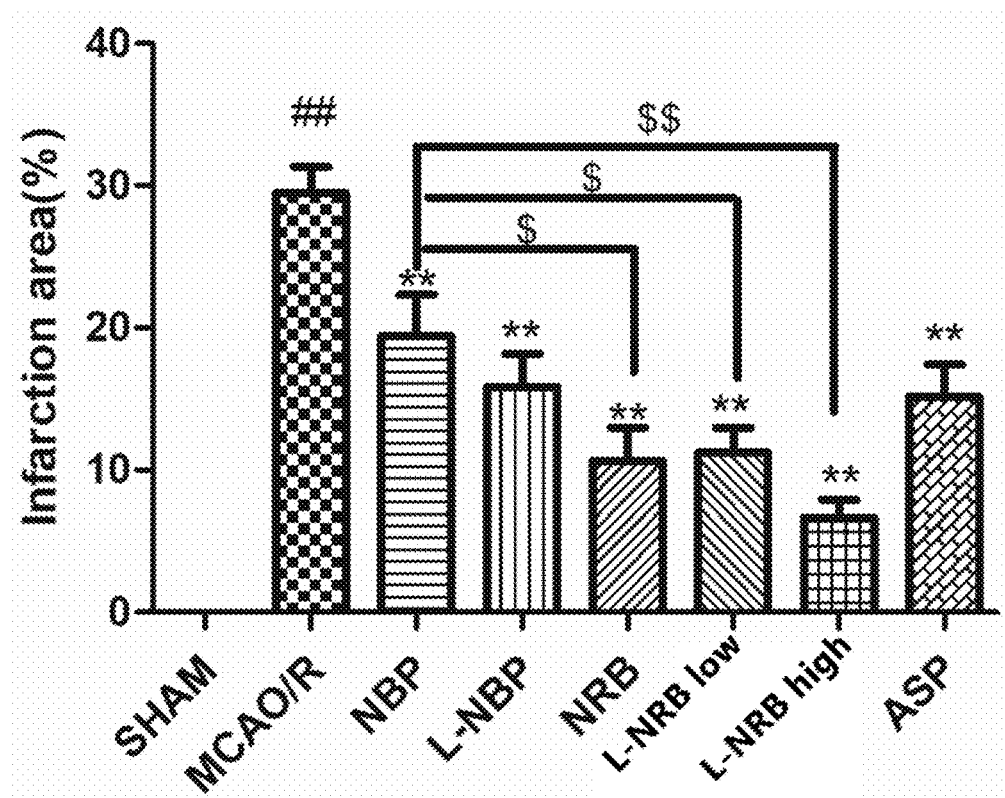
FIG. 30 demonstrates the effect of NBP derivatives on the area of cerebral infarction in rats. (# #, p<0.01 vs sham group; **, p<0.01 vs MCAO/R group; $, p<0.05 vs NBP group; $$, p<0.01 vs NBP group).
Figure 31:
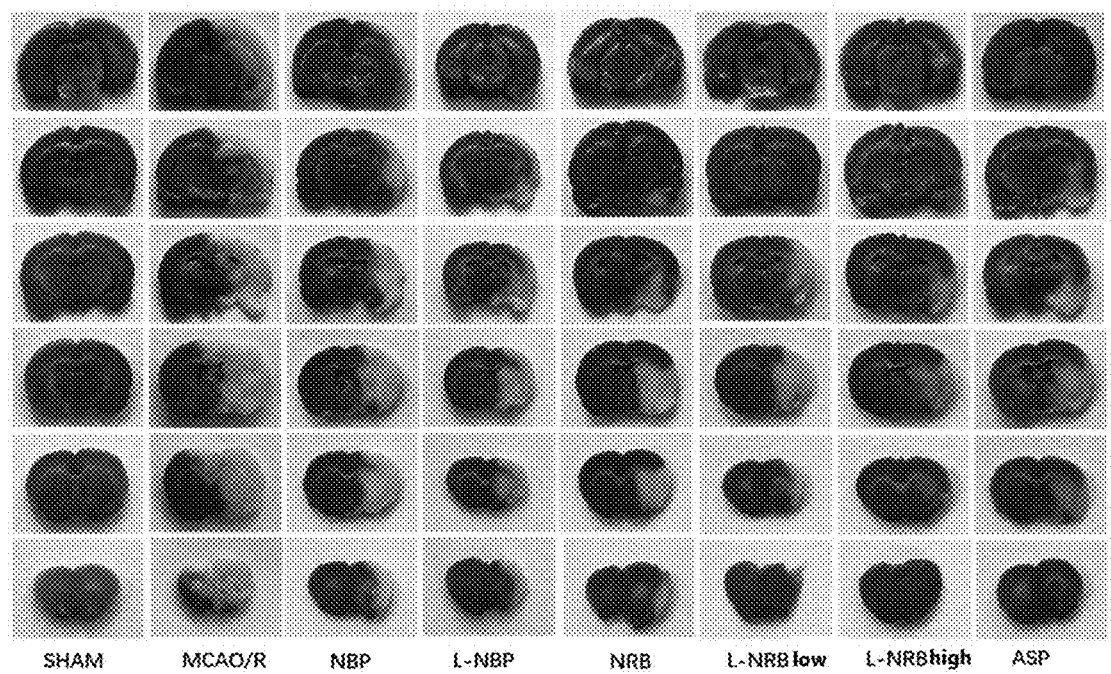
FIG. 31 is a whole brain slice photo.

The cerebral infarction area in the model group was significantly higher than that in the sham surgery group. The cerebral infarction area of each administration group was significantly lower than that of the model group ($p<0.05$). Compared with the NBP group, the NRB group ($p<0.05$), L-NRB low-dose group ($p<0.05$), and L-NRB high-dose group ($p<0.01$) showed significant reductions of cerebral infarction area (FIG. 30, FIG. 31, Table 2). The evaluation results of the evaluated derivative in reducing cerebral infarction area are consistent with the results of improving neurological function scores.

IV. Experimental Conclusion

Taking the evaluation results of improving cerebral infarction area as an example:

1. Compared with the model group, NBP group (5 mg/kg, i.e., 0.026 mmol/kg), L-NBP group (2.5 mg/kg, i.e., 0.013 mmol/kg), NRB group (15 mg/kg, i.e., 0.026 mmol/kg), L-NRB low-dose group (7.5 mg/kg, i.e., 0.013 mmol/kg), and L-NRB high-dose group (15 mg/kg, i.e., 0.026 mmol/kg) all showed activity in improving cerebral infarction area, with infarction inhibition rates (vs the model group) of 34.2%, 46.4%, 63.7%, 62.0%, and 77.6%, respectively, with significant differences. The results indicate that the hydroxypentyl benzoic acid diester compounds synthesized in this application have good therapeutic activity for cerebral ischemia, and their effects are significantly better than those of butylphthalide and levobutylphthalide.

2. Compared with NBP group, L-NBP group, NRB group, L-NRB low-dose group, and L-NRB high-dose group all showed improved cerebral infarction area activity, and the inhibition efficiency (vs NBP group) was 18.6%, 44.8%, 42.3%, and 66.0%, respectively. Moreover, there were significant differences among NRB

TABLE 2

Effect of NBP derivatives on cerebral infarction area in MCAO/R model rats

| group | Dose (mg/kg) | infarction area (%) | infarction inhibition rate (vs model group) | efficiency (vs NBP model group) | efficiency (vs L-NBP model group) | Efficiency (vs ASP model group) |
|---|---|---|---|---|---|---|
| sham surgery group | — | 0.0 ± 0.0 | — | — | — | — |
| MCAO/R model | — | 29.5 ± 5.0## | — | — | — | — |
| NBP group | 5 | 19.4 ± 7.0** | 34.2% | — | — | — |
| L-NBP group | 2.5 | 15.8 ± 6.7** | 46.4% | 18.6% | — | — |
| NRB group | 15 | 10.7 ± 7.9**$ | 63.7% | 44.8% | — | — |
| L-NRB low-dose | 7.5 | 11.2 ± 4.4**$ | 62.0% | 42.3% | 29.1% | — |
| L-NRB high-dose | 15 | 6.6 ± 3.5**$$&& | 77.6% | 66.0% | 58.2% | 56.6% |
| ASP group | 10 | 15.2 ± 7.0** | 48.5% | — | — | — |

$P < 0.01$ vs Sham surgery group;
**$P < 0.01$ vs MCAO/R model group;
$$P < 0.05$ vs NBP group;
$$$P < 0.01$ vs NBP group;
&&$P < 0.01$ vs L-NBP group group, L-NRB low-dose group, L-NRB high-dose group, and NBP group. The results showed that: 1) the activity of levorotatory butylphthalide or derivatives was superior to their corresponding racemates; 2) the activity of the butylphthalide derivative connected with two dexborneols is superior to that of the butylphthalide prototype compound.

3. Compared with L-NBP group, both L-NRB low-dose group and L-NRB high-dose group showed significant improvement in the activity of cerebral infarction area, and the inhibition efficiency (vs L-NBP group) was 29.1% and 58.2%, respectively. Moreover, there were significant differences among L-NRB low-dose group, L-NRB high-dose group and L-NBP group. These results indicate that the activity of levobutylphthalide connected with two dexborneols is better than that of levobutylphthalide prototype compound.

4. Compared with the model group, ASP group showed improved activity in cerebral infarction area, indicating the success of the model group establishment. Compared with ASP group (10 mg/kg, i.e., 0.56 mmol/kg), L-NRB high-dose group showed significant improvement in the activity of cerebral infarction area, with an inhibition efficiency of 56.6%, indicating that the hydroxypentyl benzoic acid diester compound involved in this application has a very good effect on improving the area of cerebral infarction and neurological function, which is significantly superior to the activity of aspirin, a commonly used medicine in clinical practice. It has a positive therapeutic effect in clinical practice, and has obvious medicinal properties, which is worth further development.

The above examples are only intended to illustrate the technical concept and characteristics of this application, and their purpose is to enable those skilled in the art who are familiar with this technology to understand the content of this application and implement it accordingly, and cannot limit the scope of protection of this application. Any equivalent changes or modifications made in accordance with the spirit and essence of this application shall be covered within the scope of protection of this application.

The invention claimed is:

1. A compound represented by the following formula:

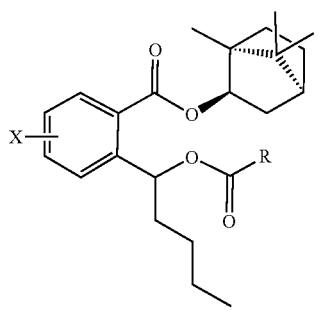

wherein R is

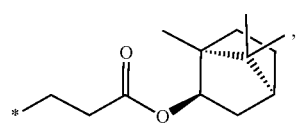

-continued

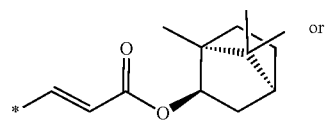

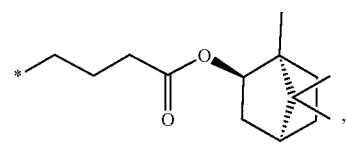

and

X is H, nitro, amino, F, Cl, Br, or I.

2. The compound as claimed in claim 1, characterized in that, the compound has the following formula:

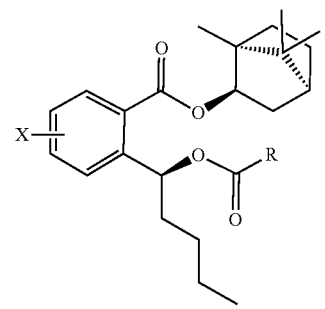

wherein R is

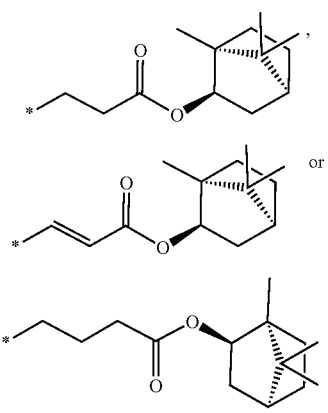

and

X is H, nitro, amino, F, Cl, Br, or I.

3. The compound as claimed in claim 1, wherein the compound is selected from the group consisting of:

25
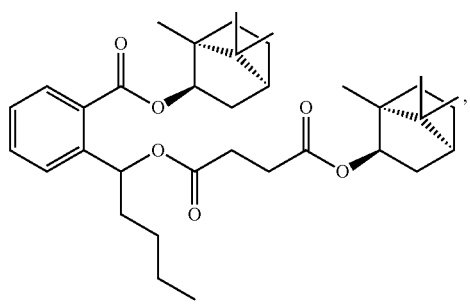
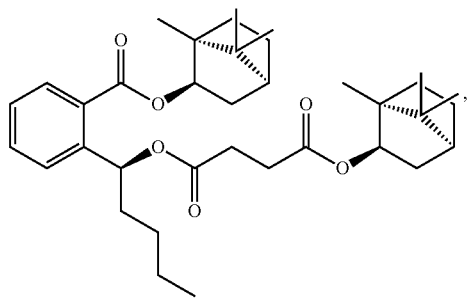
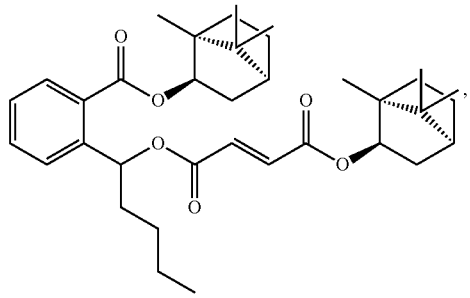
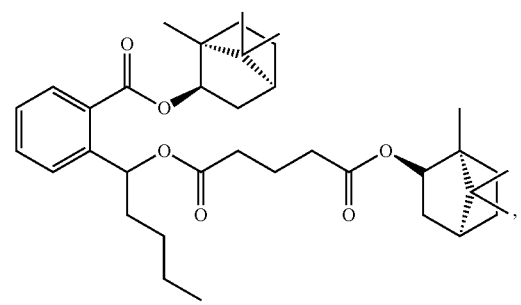
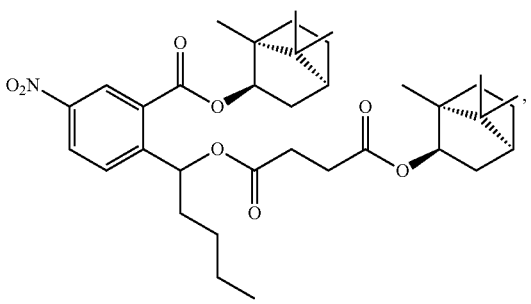
26
-continued
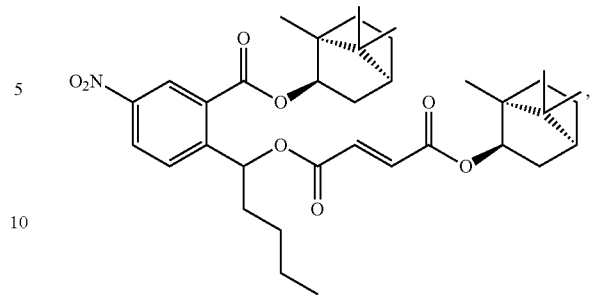
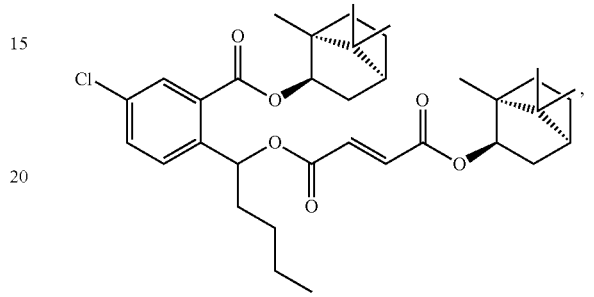
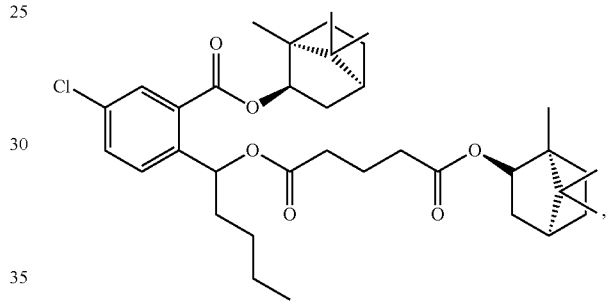
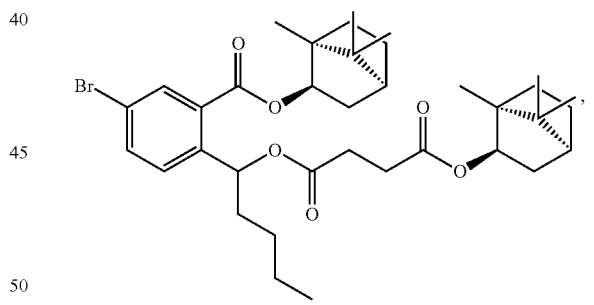
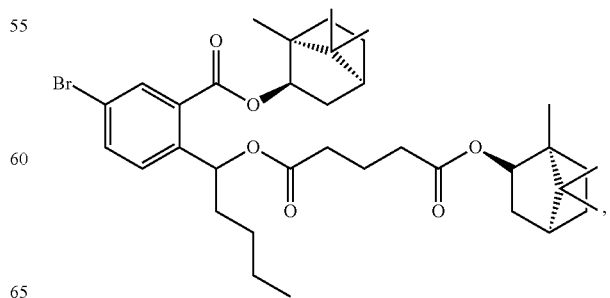

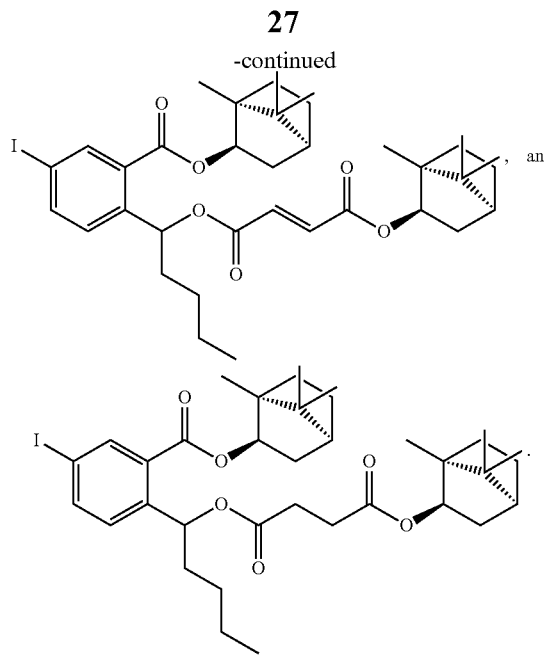

4. A pharmaceutical composition comprising the compound as claimed in claim 1 and a pharmaceutically acceptable carrier.

5. The pharmaceutical composition as claimed in claim 4, wherein the compound is the only active ingredient.

6. A pharmaceutical preparation comprising the compound as claimed in claim 1.

7. The pharmaceutical preparation as claimed in claim 6, wherein the pharmaceutical preparation is in the form of an oral dosage form, an injectable dosage form, or a transdermal dosage form.

8. The pharmaceutical composition as claimed in claim 4, wherein the pharmaceutical composition further comprises other active ingredients for treating cardio cerebral vascular disease or vascular diseases induced by senile dementia or diabetes.

9. A preparation method for the compound as claimed in claim 1, comprising the following steps:

route 1:

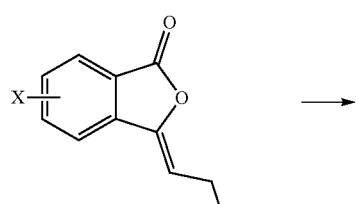

R-1

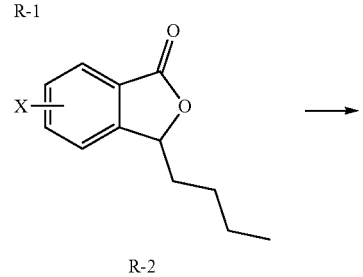

R-2

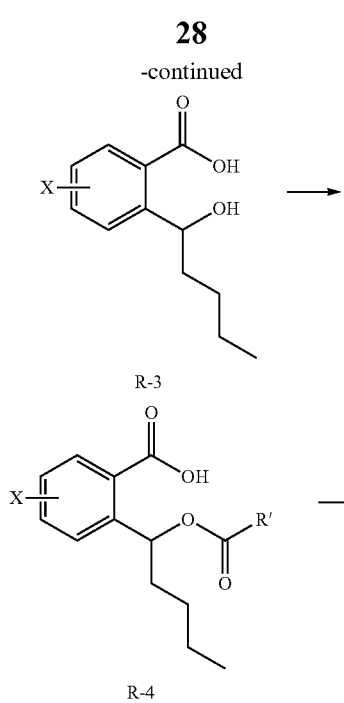

route 2:

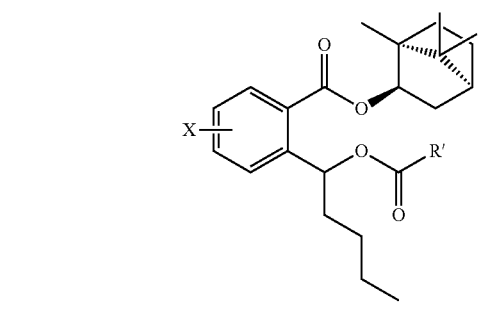

R-2

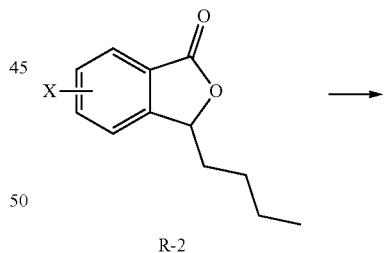

L-1

29
-continued

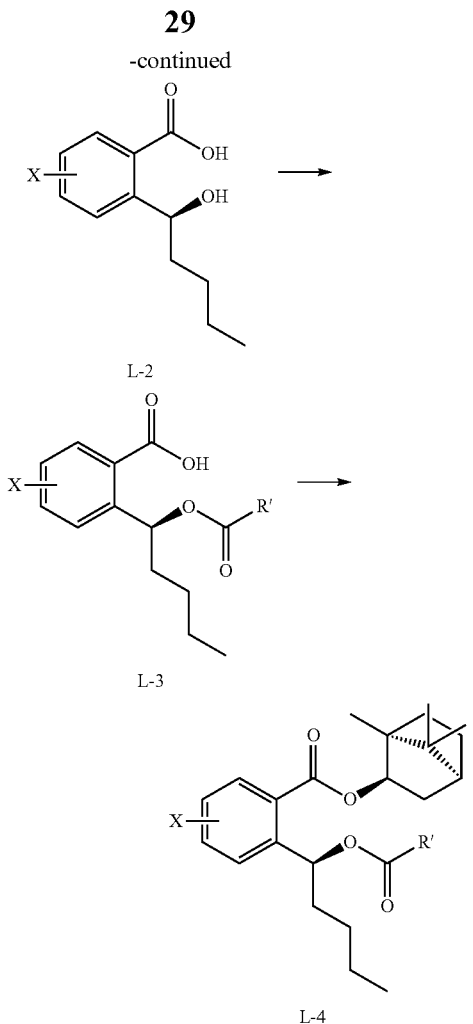

wherein R' is

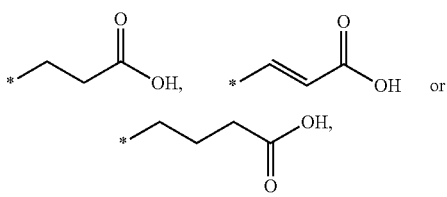

R is

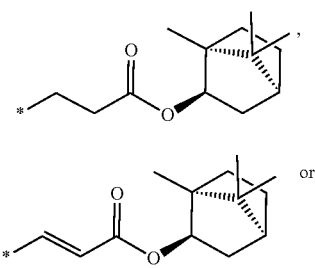

and
X is H, nitro, amino, F, Cl, Br or I;
  wherein route 1 includes the following steps:
    a). carrying out catalytic hydrogenation on butenylphthalide or substituted butenylphthalide (R-1) to reduce a double bond to obtain butylphthalide or substituted butylphthalide racemate (R-2);
    b). hydrolyzing R-2 with strong alkali under the reaction conditions selected from 1) or 2): 1) heating for reaction at a temperature of 20° C. to 120° C. for 1 hour to 5 hours; 2) carrying out microwave reaction at a temperature of 20° C. to 60° C. for 30 minutes to 1 hour; adjusting the pH to 2-4 with dilute acid after the reaction is completed, extracting with ethyl acetate or diethyl ether and concentrating to obtain an intermediate R-3; mixing R-3 sequentially with succinic anhydride, DMAP, and $Et_3N$ for reaction to obtain R-4; and
    c). performing a condensation reaction of R-4 with dexborneol catalyzed by DCC to obtain the target product R-5;
  wherein in route 2, compound R-2 is subjected to chemical chiral resolution to obtain chiral compound L-1, and then the target product L-4 is obtained by the steps b) and c).

10. The preparation method as claimed in claim 9, wherein a catalyst for the hydrogenation reaction in step a) is palladium carbon or Raney nickel.

11. The preparation method as claimed in claim 9, wherein the strong alkali in step b) is sodium hydroxide or potassium hydroxide, and a molar ratio of strong alkali to R-2 is 5:1 to 1:1.

12. The preparation method as claimed in claim 9, wherein a molar ratio of succinic anhydride to R-2 in step b) is 5:1 to 1:1; a molar ratio of $Et_3N$ to R-2 is 5:1 to 1:1; and a molar ratio of dexborneol to R-4 in step c) is 10:1 to 2:1.

13. A method for treating cardio cerebral vascular disease or vascular diseases induced by senile dementia or diabetes, comprising administering a subject in need an therapeutic effective amount of the compound as claimed in claim 1.

14. The method as claimed in claim 13, wherein the cardio cerebral vascular disease is ischemic cardio cerebral vascular disease; the vascular diseases induced by diabetes are diabetes encephalopathy, diabetes heart disease, diabetic retinopathy or diabetes nephropathy.

15. The method as claimed in claim 14, wherein the ischemic cardio cerebral vascular disease is cerebral infarction or myocardial infarction.

16. The method as claimed in claim 13, wherein the therapeutic effective amount is 7.5 mg/kg to 15 mg/kg.

17. A pharmaceutical composition comprising the compound as claimed in claim 2 and a pharmaceutically acceptable carrier.

18. A pharmaceutical composition comprising the compound as claimed in claim 3 and a pharmaceutically acceptable carrier.

19. A pharmaceutical preparation comprising the pharmaceutical composition as claimed in claim 4.

20. The pharmaceutical preparation as claimed in claim 19, wherein the pharmaceutical preparation further comprises other active ingredients for treating cardio cerebral vascular disease or vascular diseases induced by senile dementia or diabetes.

* * * * *